US010443102B2

(12) United States Patent
Rubin et al.

(10) Patent No.: US 10,443,102 B2
(45) Date of Patent: Oct. 15, 2019

(54) RECURRENT SPOP MUTATIONS IN PROSTATE CANCER

(75) Inventors: Mark A. Rubin, New York, NY (US); Christopher Barbieri, New York, NY (US)

(73) Assignee: Cornell University, Ithica, NY (US)

( * ) Notice: Subject to any disclaimer, the term of this patent is extended or adjusted under 35 U.S.C. 154(b) by 436 days.

(21) Appl. No.: 14/000,484

(22) PCT Filed: Feb. 9, 2012

(86) PCT No.: PCT/US2012/024475
§ 371 (c)(1),
(2), (4) Date: Aug. 20, 2013

(87) PCT Pub. No.: WO2012/115789
PCT Pub. Date: Aug. 30, 2012

(65) Prior Publication Data
US 2013/0331279 A1 Dec. 12, 2013

Related U.S. Application Data

(60) Provisional application No. 61/446,255, filed on Feb. 24, 2011, provisional application No. 61/467,735, filed on Mar. 25, 2011.

(51) Int. Cl.
*C12Q 1/6886* (2018.01)
*G01N 33/574* (2006.01)

(52) U.S. Cl.
CPC ..... *C12Q 1/6886* (2013.01); *G01N 33/57434* (2013.01); *G01N 33/57484* (2013.01); *C12Q 2600/112* (2013.01); *C12Q 2600/156* (2013.01)

(58) Field of Classification Search
None
See application file for complete search history.

(56) References Cited

U.S. PATENT DOCUMENTS

| 5,807,681 | A * | 9/1998 | Giordano | C07K 14/4736 435/6.16 |
| 7,666,607 | B1 | 2/2010 | Zapata et al. | |
| 2002/0165345 | A1 * | 11/2002 | Cohen | C07K 14/47 530/350 |
| 2003/0092019 | A1 * | 5/2003 | Meyer | C07K 14/47 435/6.14 |
| 2003/0175736 | A1 | 9/2003 | Chinnaiyan et al. | |
| 2004/0053247 | A1 | 3/2004 | Cordon-Cardo et al. | |
| 2010/0092984 | A1 | 4/2010 | Liew | |
| 2011/0236903 | A1 | 9/2011 | McCelelland et al. | |
| 2011/0275528 | A1 | 11/2011 | Meyer et al. | |

FOREIGN PATENT DOCUMENTS

| WO | 2008/086502 A2 | 7/2008 |
| WO | 2010/065940 A1 | 6/2010 |
| WO | 2010/102277 A2 | 9/2010 |
| WO | 2013/072393 A2 | 5/2013 |

OTHER PUBLICATIONS

Berger (Nature vol. 470 pp. 214-220 Feb. 10, 2011).*
Kan (Nature vol. 466 Aug. 2010 pre-published online Jul. 28, 2010).*
Yoshimoto (Modern Pathology 2008 vol. 21 pp. 1451-1460).*
Hegele (Arterioscler Throm Vasc Biol 2002 vol. 22 pp. 1058-1061).*
Lucentini (The Scientist 2004 vol. 18 pp. 1-3).*
Mummidi et al (Journal of Biological Chemistry 2000 vol. 275 No. 25 pp. 18946-18961).*
Berger, M.F. et al., "The genomic complexity of primary human prostate cancer" Nature (Feb. 10, 2011) pp. 214-220, vol. 470.
Bhatia-Gaur, R. et al., "Roles for Nkx3.1 in prostate development and cancer" Genes Dev. (1999) pp. 966-977, vol. 13.
Boormans, J.L. et al., "E17K substitution in AKT1 in prostate cancer" Br J Cancer (2010) pp. 1491-1494, vol. 102, No. 10.
Cairns, P. et al., "Frequent Inactivation of PTEN/MMAC1 in Primary Prostate Cancer" Cancer Res. (1997) pp. 4997-5000, vol. 57.
Carver, B.S. et al., "Aberrant ERG expression cooperated with loss of PTEN to promote cancer progression in the prostate" Nat. Genet. (May 2009) pp. 619-624, vol. 41, No. 5.
Chapman, M.A. et al., "Initial genome sequencing and analysis of multiple myeloma" Nature (Mar. 24, 2011) pp. 467-472, vol. 471.
Demichelis, F. et al., "Distinct Genomic Aberrations Associated with ERG Rearranged Prostate Cancer" Genes Chromosomes Cancer (2009) pp. 366-380, vol. 48.
Forbes, S.A. et al., "COSMIC: mining complete cancer genomes in the catalogue of somatic mutations in cancer" Nucleic Acids Res. (2011) pp. D945-D950, vol. 39.
Gao, L. et al., "Epigenetic regulation of androgen receptor signaling in prostate cancer" Epigenetics (2010) pp. 100-104, vol. 5, No. 2.
He, W.W. et al., "A Novel Human Prostate-Specific, Androgen-Regulated Homeobox Gene (NKX3.1) That Maps to 8p21, a Region Frequently Deleted in Prostate Cancer" Genomics (1997) pp. 69-77, vol. 43.
Kan, Z. et al., "Diverse Somatic Mutation Patterns and Pathway Alterations in Human Cancers" Nature (Aug. 12, 2010) pp. 869-875, vol. 466.
Kibel, A.S. et al., "CDKN1A and CDKN1B Polymorphisms and Risk of Advances Prostate Carcinoma" Cancer Res. (2003) pp. 2033-2036, vol. 63.
King, J.C. et al., "Cooperativity of TMPRSS2-ERG with PI3-kinase pathway activiation in prostate oncogenesis" Nat. Genet. (May 2009) pp. 524-526, vol. 41, No. 5.
Lapointe, J. et al., "Genomic Profiling Reveals Alternative Genetic Pathways of Prostate Tumorigenesis" Cancer Res. (Sep. 15, 2007) pp. 8504-8510, vol. 67, No. 18.

(Continued)

*Primary Examiner* — Amanda Haney
(74) *Attorney, Agent, or Firm* — Scully Scott Murphy & Presser, P.C.

(57) ABSTRACT

The invention relates generally to new prostate cancer markers, and particularly to a class of cancer marked by the presence of missense mutations in SPOP, an E3 ubiquitin ligase component. The invention provides methods and materials for detecting and diagnosing prostate cancer by detecting these mutations and may be useful in predicting disease progression and response to therapy.

21 Claims, 10 Drawing Sheets

Specification includes a Sequence Listing.

(56) References Cited

OTHER PUBLICATIONS

Li, J. et al., "PTEN, a Putative Protein Tyrosine Phosphatase Gene Mutated in Human Brain, Breast, and Prostate Cancer" Science (Mar. 28, 1997) pp. 1943-1947, vol. 275.

Linja, M.J. et al., "Alterations of Androgen receptor in prostate cancer" J. Steroid Biochem. Mol. Biol. (2004) pp. 255-264, vol. 92.

Liu, J. et al., "Analysis of *Drosophila* Segmentation Network Identified a JNK Pathway Factor Overexpressed in Kidney Cancer" Science (Jan. 22, 2009) pp. 1218-1826, vol. 323.

Majumder, P.K. et al., "A Prostatic Intraepithelial Neoplasia-Dependent p27Kip1 Checkpoint Induces Senescence and Inhibits Cell Proliferation and Cancer Progression" Cancer cell (Aug. 12, 2008) pp. 146-155, vol. 14.

Mandelbaum, J. et al., "BLIMP1 Is a Tumor Suppressor Gene Frequently Disrupted in Activated B Cell-like Diffuse Large B Cell Lymphoma" Cancer Cell (Dec. 14, 2010) pp. 568-579, vol. 18.

Mosquera, J.-M. et al. "Prevalence of TMPRSS2-ERG Fusion Prostate Cancer among Men Undergoing Prostate Biopsy in the United States" Clin. Cancer Res. (Jul. 15, 2009) pp. 4706-4711, vol. 15.

Nagai, Y. et al., "Identification of a novel nuclear speckle-type protein, SPOP" FEBS Lett. (1997) pp. 23-26, vol. 418.

Perner, S. et al., "TMPRSS2:ERG Fusion-Associated Deletions Provide Insight into the Heterogeneity of Prostate Cancer" Cancer Res.(Sep. 1, 2006) pp. 8337-8341, vol. 66, No. 17.

Rubin, M.A. et al., "Rapid ("Warm") Autopsy Study for Procurement of Metastatic Prostate Cancer" Clin. Cancer Res. (Mar. 2000) pp. 1038-1045, vol. 6.

Stransky, N. et al., "The Mutational Landscape of Head and Neck Squamous Cell Carcinoma" Science (Aug. 26, 2011) pp. 1157-1158, vol. 333.

Taylor, B.S. et al., "Integrative Genomic Profiling of Human Prostate Cancer" Cancer Cell (Jul. 11-22, 2010) pp. 11-22, vol. 18.

Tomlins, S.A. et al., "Distinct classes of Chromosomal rearrangements create oncogenic ETS gene fusions in prostate cancer" Nature (Aug. 2, 2007) pp. 595-601, vol. 448.

Tomlins, S.A. et al., "Recurrent Fusion of TMPRSS2 and ETS Transcription Factor Genes in Prostate Cancer" Science (Oct. 28, 2005) pp. 644-648, vol. 310.

Visakorpi, T. et al., "In vivo am,plication of the androgen receptor gene and progression of human prostate cancer" Nat. Genet (Apr. 1995) pp. 401-406, vol. 9.

Yang, J.-Y. et al., "A New Fork for Clinical Application: Targeting Forkhead Transcription Factors in Cancer" Clin Cancer Res (2009) pp. 752-757, vol. 15.

Zhuang, M. et al., "Structures of SPOP-Substrate Complexes: Insights into Molecular Architectures of BTB-Cul3 Ubiquitin Ligases" Mol. Cell. (Oct. 9, 2009) pp. 39-50, vol. 36.

Barbieri, C.E. et al., "Molecular Genetics of Prostate Cancer: Emerging Appreciation of Genetic Complexity" Histopathology (Jan. 1, 2012) pp. 187-198, vol. 60, No. 1.

International Search Report dated Sep. 26, 2012 issued in International Application No. PCT/US2012/024475.

Brenner, J. et al., "Disruptive Events 1-16 in the Life of Prostate Cancer" Cancer Cell (Mar. 2011) pp. 301-303, vol. 19, No. 3.

Grönberg, H., "Submitted SNP(ss) Details: ss472334310 clinically associated" *dbSNP* (Nov. 2011) pp. 1-2.

Ding, Z. et al., "SMAD4-dependent barrier constrains prostate cancer growth and metastatic progression" *Nature* (Feb. 2011) pp. 269-273, vol. 470, No. 7333.

Barbieri, C.E. et al., "Exome sequencing identifies recurrent SPOP, FOXAl and MED12 mutations in prostate cancer" *Nature Genetics* (May 2012) pp. 685-689, vol. 44, No. 6.

Supplementary European Search Report issued in European Application No. EP 12750231.8 dated Jun. 30, 2015.

\* cited by examiner

SEQUENCE LISTING

<160> NUMBER OF SEQ ID NOS: 14

<210> SEQ ID NO 1
<211> LENGTH: 19
<212> TYPE: DNA
<213> ORGANISM: Artificial Sequence
<220> FEATURE:
<223> OTHER INFORMATION: Synthetic Oligonucleotide primer

<400> SEQUENCE: 1
ttctatgggg cctgcattt                                                   19

<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide primer

<400> SEQUENCE: 2
ctccacttgg ggcttttct                                                  20

<210> SEQ ID NO 3
<211> LENGTH: 22
<212> TYPE: DNA
<213> ORGANISM: Artificial Sequence
<220> FEATURE:
<223> OTHER INFORMATION: Synthetic Oligonucleotide primer

<400> SEQUENCE: 3
ttttctatct gttttggaca gg                                              22

<210> SEQ ID NO 4
<211> LENGTH: 21
<212> TYPE: DNA
<213> ORGANISM: Artificial Sequence
<220> FEATURE:
<223> OTHER INFORMATION: Synthetic Oligonucleotide primer

<400> SEQUENCE: 4
caaagccaca acttgtcagt g                                               21

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide primer

<400> SEQUENCE: 5
tttgcgagta aacccaaag                                                  20

<210> SEQ ID NO 6
<211> LENGTH: 21
<212> TYPE: DNA
<213> ORGANISM: Artificial Sequence

```
<220> FEATURE:
<223> OTHER INFORMATION: Synthetic Oligonucleotide primer

<400> SEQUENCE: 6
ctcatcagat ctgggaactg c                                              21

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide primer

<400> SEQUENCE: 7
cttctgcgag gtgagtgttg                                                20

<210> SEQ ID NO 8
<211> LENGTH: 21
<212> TYPE: DNA
<213> ORGANISM: Artificial Sequence
<220> FEATURE:
<223> OTHER INFORMATION: Synthetic Oligonucleotide primer

<400> SEQUENCE: 8
tcccacagtc ctcctaactc a                                              21

<210> SEQ ID NO 9
<211> LENGTH: 20
<212> TYPE: DNA
<213> ORGANISM: Artificial Sequence
<220> FEATURE:
<223> OTHER INFORMATION: Synthetic Oligonucleotide primer

<400> SEQUENCE: 9
tgcaccacca actgcttagc                                                20

<210> SEQ ID NO 10
<211> LENGTH: 21
<212> TYPE: DNA
<213> ORGANISM: Artificial Sequence
<220> FEATURE:
<223> OTHER INFORMATION: Synthetic Oligonucleotide primer

<400> SEQUENCE: 10
ggcatggact gtggtcatga g                                              21

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide primer

<400> SEQUENCE: 11
acaaactcct ggtgcaaacc                                                20

<210> SEQ ID NO 12
<211> LENGTH: 20
<212> TYPE: DNA
<213> ORGANISM: Artificial Sequence
<220> FEATURE:
<223> OTHER INFORMATION: Synthetic Oligonucleotide primer

<400> SEQUENCE: 12
aagcgctggg attaatgatg                                                20
```

```
<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide primer

<400> SEQUENCE: 13
atcagggagg aaagcagact                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide primer

<400> SEQUENCE: 14
tgtctgtatt ggctgcactc                                              20
```

RECURRENT SPOP MUTATIONS IN PROSTATE CANCER

CROSS-REFERENCE TO RELATED APPLICATIONS

This application claims priority to under 35 U.S.C. § 119(e) to provisional applications U.S. Ser. No. 61/446,255, filed Feb. 24, 2011, and U.S. Ser. No. 61/467,735, filed Mar. 25, 2011, each of which is incorporated herein in its entirety.

FIELD OF THE INVENTION

The invention relates generally to new prostate cancer markers, and particularly to a class of cancer marked by the presence of missense mutations in SPOP, an E3 ubiquitin ligase component. The invention provides methods and materials for detecting and diagnosing prostate cancer by detecting these mutations and may be useful in predicting disease progression and response to therapy.

INCORPORATION BY REFERENCE OF SEQUENCE LISTING

The Sequence Listing in an ASCII text file, named as 27370_5368_04_SequenceListing.txt of 4 KB, created on Aug. 13, 2013, and submitted to the United States Patent and Trademark Office via EFS-Web, is incorporated herein by reference.

BACKGROUND OF THE INVENTION

Prostate cancer is a clinically heterogeneous disease with marked variability in outcomes. It is the second most common cancer in men worldwide and causes over 250,000 deaths each year (JEMAL (2011)). Yet, overtreatment of indolent disease also results in significant morbidity (DASKIVICH 2011). A deeper understanding of the molecular pathogenesis of prostate cancer is needed to guide the deployment of new therapies and to distinguish benign from aggressive disease. Common genetic alterations in prostate cancer include losses of NKX3.1 (8p21) (HE (1997), BHATIA-GAUR (1999)) and PTEN (10q23) (LI (1997), CAIRNS (1997)), gains of the androgen receptor gene (AR) (LINJA (2004), VISAKORPI (1995)) and fusion of ETS-family transcription factor genes with androgen-responsive promoters (PERNER (2006), TOMLINS (2007), TOMLINS (2005)). These discoveries raise the possibility that prostate cancer might soon transition from a poorly understood, clinically heterogeneous disease to a collection of homogenous subtypes identifiable by molecular criteria.

In contrast to the well-defined genomic lesions in prostate cancer, protein-altering point mutations are uncommon. The overall and protein-altering mutation rate of primary prostate cancer is among the lowest reported, approximately an order of magnitude lower than other cancers (BERGER (2011), KAN (2010)). Consistent with this, recurrent protein-altering mutations are rare in prostate cancer. Mutations in AR, PTEN, and AKT1 are among the most common (FORBES (2011), BOORMANS (2010)); these occur rarely in primary prostate cancer, with reported frequency around 1% (TAYLOR (2010)). Accordingly, this study examined the point mutations present in a large cohort of prostate cancer patients and discovered recurrent mutations in the substrate binding cleft of SPOP in the cohort were associated with a distinct molecular subtype of prostate cancer.

SUMMARY OF THE INVENTION

Prostate cancer is a common and clinically heterogeneous malignancy. The present invention relates to the discovery that recurrent SPOP mutations are associated with a distinct subtype of prostate cancer. This subtype of prostate cancer is also correlated with a lack of ETS-fusions and other co-occurring genomic alterations as described herein. Accordingly, the invention provides a method for genotyping prostate cancer in a patient by detecting the SPOP mutation profile in a prostate sample from the patient, wherein the presence of a mutation in the MATH domain of SPOP correlates with this specific genotype of prostate cancer. Thus cancer samples with a mutation in the SPOP domain represent a distinct subtype of prostate cancer, and have a genotype which may include being is ERG-fusion/ETS-fusion negative as well as genomic deletion in the 5q21 or the 6q21 regions. The specific SPOP mutations that have been observed in the present invention are missense mutations at amino acids at positions Y87, F102, S119, F125, K129, W131, F133 or K134 of SPOP. Generally only single missense mutations have been observed in each sample. Other mutations in the MATH domain are contemplated provided they are deleterious to the activity of the SPOP MATH domain, which is associated with substrate binding.

Suitable samples in which to detect the SPOP mutations using the methods of the invention include, but are not limited to, prostate tissue, urine, semen, a prostatic secretion, or prostate cells. These samples can be in any form, for example, obtained directly from a biopsy or other sampling technique or having been preserved by a fixation and paraffin embedding technique.

Methods of determining the identity of a mutation in a nucleic acid sample are varied and well known in the art, and include different types of sequencing such as pyrosequencing, next generation sequencing, and Sanger sequencing. Mutations can also be detected by hybridization with oligonucleotides probes using in situ hybridization techniques or by other techniques such as RT-PCR, blotting or using microarrays based techniques. Probe design for missense mutations in the MATH domain of SPOP is within the ken of the art. Accordingly, one embodiment of invention is directed to methods for detecting mutations amplifying an SPOP-containing nucleic acid fragment in a sample and sequencing the amplified nucleic acid to identify the presence of a mutation. The fragment may contain all of SPOP, or any region of SPOP that includes the MATH domain, or can consist essentially of the MATH domain. The MATH domain extends from about amino acid 78 to about amino acid 144 of SPOP from most species (being a highly conserved domain). In another embodiment, the SPOP mutation is detected in situ, typically by in situ hybridization. In a further embodiment, the SPOP mutation is detected by obtaining nucleic acid from a sample using a microarray-based assay or an RT-PCR-based assay.

Another aspect of the invention relates to method of diagnosing prostate cancer by detecting the presence of a mutation in the MATH domain of SPOP from a prostate sample, wherein presence of a mutation indicates the patient has prostate cancer. This method can further include determining the presence or absence of one or more co-occurring genomic alterations. Such genomic alterations include, but are not limited to, the absence of a PTEN mutation, the absence of PTEN copy number loss, the presence of a 5q21 deletion, the presence of a 6q21 deletion or the absence of an ETS-rearrangement, or any combination thereof. Again, the observed SPOP mutations are missense mutations at least one of the amino acids at positions Y87, F102, S119, F125, K129, W131, F133 or K134 of SPOP. Mutation detection is as described above.

Another embodiment of the invention is directed to stratifying a patient into a subtype of prostate cancer by determining the genotype of the SPOP MATH domain and the ETS-rearrangements in the nucleic acids obtained from prostatic tissue wherein a genotype of missense mutations in the MATH domain at amino acids Y87, F102, S119, F125, K129, W131, F133 or K134 of SPOP and being ETS-rearrangement negative enables stratification of said patient into a subtype of prostate cancer.

In a still further aspect, the invention provides prostate cancer screening kits. These kits can be configured in many ways but share a common feature of providing nucleic acids, e.g., oligonucleotides or primers to enable specific detection of the SPOP MATH domain mutations in the nucleic acid found in a prostate sample. For example, in one format, the kit comprises SPOP-specific oligonucleotides to amplify nucleic acid obtained from a prostate sample, and, optionally, primer or adapters suitable to enable sequencing of the amplified nucleic acid and determination of the presence of a mutation in the MATH domain of SPOP. The SPOP-specific oligonucleotides may be designed to amplify the MATH domain and further to be specific for detection of missense mutations in the MATH domain of SPOP. In another embodiment, a kit of the invention can have said one or more oligonucleotides are adapted for use in an in situ hybridization format or for use in a microarray format for identifying mutations.

Any of the foregoing kits, as appropriate can contain oligonucleotides, primers or other reagents specifically needed for amplifying, sequencing and/or detecting another prostate cancer biomarker, including biomarkers such an ETS-rearrangement, a PTEN mutation, a PTEN deletion, and an ERG-fusion. The kits may further contain reagents for detecting copy number variation (CNV) in the 5q21 and/or 6q21 genomic loci.

DETAILED DESCRIPTION OF THE INVENTION

Figure 1:
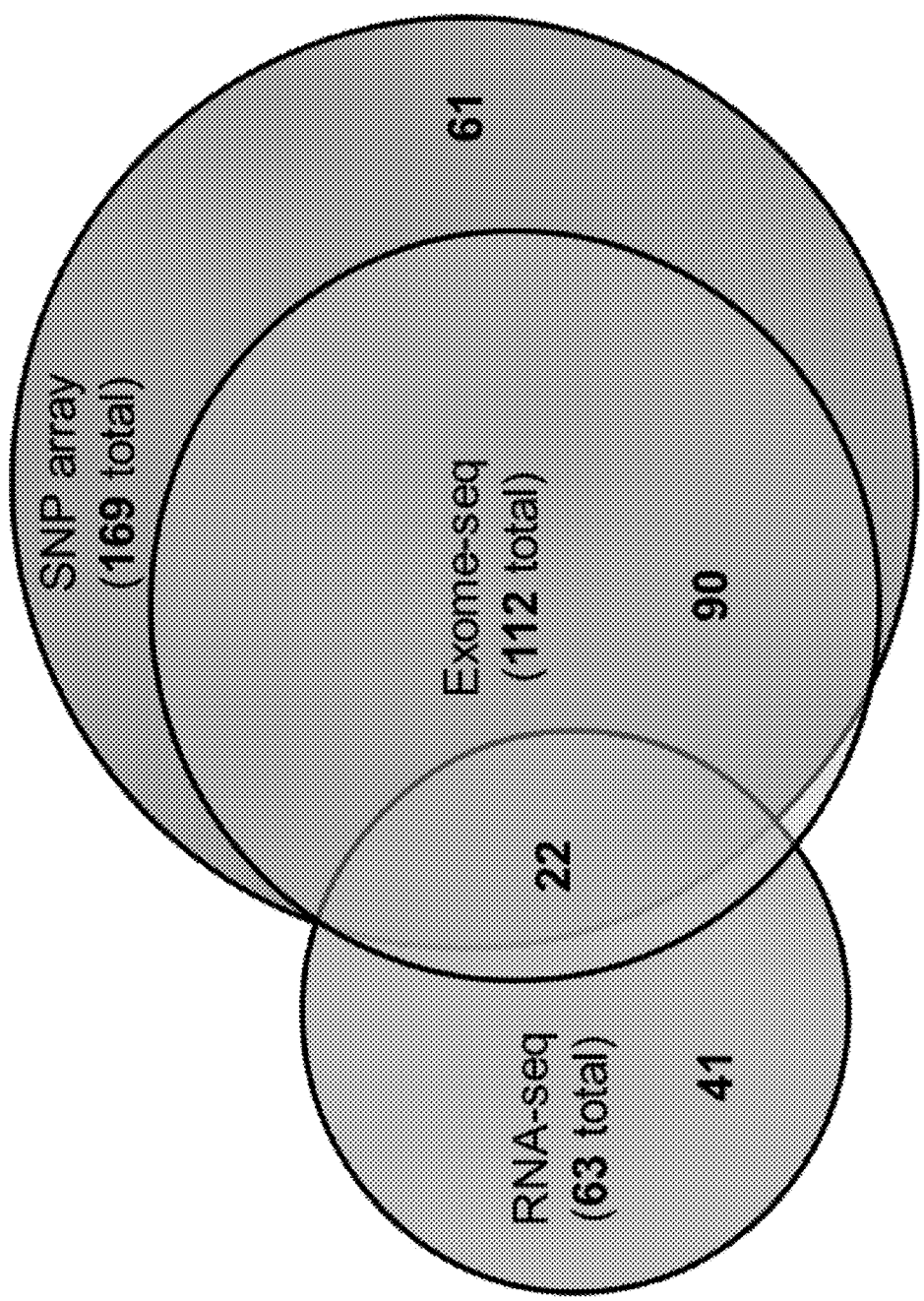
FIG. 1. Overlap of sample profiling across platforms. Exome sequencing was conducted on 112 tumor-normal pairs. A single highly-mutated tumor was excluded from subsequent analyses, except where otherwise indicated, leaving 111 pairs FIG. 2. Significantly mutated genes in aggressive primary prostate cancer. (Center) Mutations in significantly mutated genes. Each column represents a tumor and each row a gene. (Left) Number and percentage of tumors with mutations in a given gene. (Right) The negative log of the q-values for the significance level of mutated genes is shown (for all genes with q<0.1).

To determine the frequency and positional distribution of SPOP mutations in prostate cancer, the SPOP coding region in RNA-seq data from prostate adenocarcinoma samples was initially examined. SPOP mutations were then further examined in multiple independent cohorts, with mutations involving the SPOP substrate binding cleft (which is part of the MATH domain) being found in 6-15% of the tumors across those cohorts. SPOP-mutant prostate cancers lacked ETS rearrangements and exhibited a distinct pattern of genomic alterations. Thus, SPOP mutations define a new molecular subtype of prostate cancer.

Accordingly, the present invention is directed to a method for genotyping prostate cancer in a patient by detecting the SPOP mutation profile for nucleic acid in a prostate tissue sample or other sample containing prostate-derived cells or secretions, from the patient. The SPOP mutations associated with prostate cancer are found in the MATH domain of SPOP and these mutations represent a distinct subtype of prostate cancer.

SPOP is a nuclear speckle-type POZ protein and that has transcriptional repression activity and ubiquitin ligase activity (as part of a multiprotein complex). The MATH domain of SPOP has been shown to bind substrates destined for ubiquitination (18). The BTB/POZ domain of this protein has been shown in other proteins to mediate transcriptional repression and to interact with components of histone deacetylase co-repressor complexes. The human SPOP gene, according to the UCSC annotation system, is located at chr17:47676245-47755525.

As used herein "the SPOP mutation profile" means any mutation found in the SPOP MATH domain as identified herein or any other mutation located in the MATH domain which may be deleterious to SPOP activity such as substrate binding for transcriptional repression activity. Examples of the former group of mutations found in SPOP are missense mutations at the nucleotide level which lead to changed amino acids at positions Y87, F102, S119, F125, K129, W131, F133 or K134 in SPOP (see examples in FIG. 3A, Table 3 and Table 5). These mutations are likely to adversely affect SPOP function (and at least one has been shown to) and this correlates with increased oncogenic potential of the mutated cells as shown in Example 3. Generally only one mutation is present per sample, but this need not be the case Methods for detecting the SPOP mutation profile in a sample are varied and can involve extracting the nucleic acids from a prostate sample or involve direct in situ hybridization to the sample. A tissue sample can be obtained by a biopsy, from tissue obtained during a radical prostatectomy or even laser excised from a histological-stained and preserved tissue sample. Tissues may also be obtained from metastases to non-prostatic tissues if present. Further, suitable sample sources for use in the detection are biological specimens which contain prostate-derived cells or secretions and include, but are not limited to, prostate tissue, urine, semen, prostatic secretions and prostate cells. In a specific embodiment, a urine sample can be collected immediately following a digital rectal examination (DRE), which often causes prostate cells from the prostate gland to shed into the urinary tract. Samples can be further processed to enrich for prostate-specific cells or other material having prostate-derived nucleic acids associated with it. Nucleic acids can be obtained from these samples by extraction or other methods using known techniques and can be amplified if needed for the detection method being used. Nucleic acids can also be preserved in the sample by fixation or other techniques used to prepare a sample for in situ hybridization.

The nucleic acids can be any kind of RNA or DNA, and RNA can be converted to cDNA if desired. For example, the SPOP gene can be specifically amplified via PCR and the resultant amplification products subjected to sequencing analysis to thereby identify the SPOP mutations. One of skill in the art can determine the appropriate primers for amplifying the SPOP coding sequence. In some embodiments, in may be preferable to amplify the MATH domain of SPOP. Examples of SPOP primers are shown in Table 2. A myriad of amplification and sequencing techniques are known and available in the art (see, e.g., focused genotyping, bead chips, and the next generation sequencing provided by Illumina or the 454 pyrosequencing provided by Roche), and any combination can be performed to identify the SPOP mutations. SPOP mutations can also be detected on microarrays that have an appropriate set of probes to identify missense mutations in the MATH domain (e.g., using techniques similar to those used for SNP detection and other genotyping techniques). Other detection methods include in situ hybridization techniques using oligonucleotides and hybridization conditions that discriminate between missense mutations and wild-type sequences in the SPOP MATH domain. Such oligonucleotides and hybridization conditions can be determined by those of skill in the art.

As another method for detecting SPOP mutations, antibodies can be used to detect mutant SPOP proteins present in a prostate sample or other sample (e.g., in blood, serum or other body fluid).

In addition, to determining the SPOP genotype in cancerous prostate tissue, the nucleic acids can be assayed and analyzed for the presence of ETS-rearrangements and other genomic alterations using methods known in the art. While these assays can be performed with prostate-specific samples, they do not necessarily need prostate-specific samples since these biomarkers have been observed in non-prostatic tissues. Hence, blood, urine and other readily available sources of genomic or other nucleic acids from a patient can be used. SPOP-mutant prostate cancers lack ETS rearrangements and exhibit a distinct pattern of genomic alterations, including copy number aberrations in the 5q21 and/or the 6q21 regions (with deletions and copy number loss being correlated with the presence of SPOP mutations). The loss of tumor-suppressor genes in the 5q21 and 6q21 regions may collaborate with SPOP mutation to promote tumorigenesis.

Other co-occurring genomic alterations may include the absence of a PTEN mutation or the absence of PTEN copy number loss.

Another aspect of the invention is directed to a method of diagnosing prostate cancer by detecting the presence of a missense mutation in the MATH domain of SPOP in a nucleic acid from a prostate tissue sample such that the presence of the mutation is indicative that the patient has prostate cancer, and particularly the subtype of prostate cancer associated with recurrent SPOP mutations. Detection of the mutations is accomplished as described for genotyping.

Additionally, the method of diagnosis may include determining the presence or absence of one or more co-occurring genomic alterations. The presence of these alterations, particularly, in conjunction with the lack of ETS-rearrangements appears to indicate a poor prognosis for prostate cancer.

The co-occurring genomic alterations that have been observed in patients with recurrent SPOP mutations include the presence of a 5q21 deletions (or copy number loss), the presence of a 6q21 deletions (or copy number loss), the absence of an ETS-rearrangement, the absence of a PTEN mutation, the absence of PTEN copy number loss and combinations thereof.

In some embodiments, the methods of the invention can be used to stratify a patient into a subtype of prostate cancer which comprises determining the genotype of the SPOP MATH domain and the ETS-rearrangements in the nucleic acids obtained from prostatic tissue, wherein a genotype of missense mutations in the MATH domain at amino acids Y87, F102, S119, F125, K129, W131, F133 or K134 and being ETS-rearrangement negative enables stratification of said patient into a subtype of prostate cancer. By knowing SPOP mutation status, the clinician may be able to predict or determine a patient's response to therapy, including surgery, radiation, chemotherapy or targeted pharmacologic therapy.

A further aspect of the invention is directed to prostate cancer screening kits for detecting SPOP mutations. Such kits can take many forms, for example, one type of kit is designed for sequencing nucleic acid obtained from a prostate tissue sample to determine whether mutations are present in the MATH domain of SPOP. Such a kit can contain SPOP-specific primers to amplify the nucleic acid (either RNA or DNA) and further primers to sequence the RNA or DNA depending on the sequence technique to be used. Sequencing techniques are well known in the art. Moreover, the kit may optionally contain primers for amplifying, sequencing and detecting other prostate cancer biomarkers, including such markers as PTEN mutations, PTEN deletions, ETS-rearrangement status and ERG-fusions. Further the kits of the invention can be combined with reagents for detecting copy number variation (CNV) at specific genetic loci associated with prostate cancer, including, but not limited to, deletions at the 5q21 and 6q21 loci.

In another embodiment, the prostate cancer screening kit can be in a microarray format designed for detection of specific mutations in the MATH domain of SPOP. For example, the microarray can be designed for a somatic mutation PCR array procedure in which genomic DNA is isolated and amplified from prostate tissue. The mutations are detected on a microarray system containing SPOP MATH domain mutant-specific primer and hydrolysis probe sets by performing real-time PCR. Hence, the kit contains a microarray of SPOP MATH domain mutant-specific primer and hydrolysis probe sets (and appropriate controls) that can detect nucleotide changes that lead to missense mutations at positions Y87, F102, S119, F125, K129, W131, F133 or K134 of SPOP. Hence the present invention includes PCR arrays for detecting the forgoing mutations. Specific primers and probes can be designed by those of skill in the art.

In summary, next generation sequencing identified a distinct ETS fusion-negative subclass of prostate cancer characterized by recurrent SPOP mutations and enriched for both 5q21 and 6q21 deletions. This expanded genetic framework may articulate new mechanisms of carcinogenesis that inform both disease modeling and patient stratification for clinical trials of experimental agents. Together with additional comprehensive analyses of the prostate cancer genome, epigenome, and transcriptome, these systematic approaches should illuminate the landscape of alterations that underlie disease biology and therapeutic vulnerability in this common and clinically heterogeneous malignancy.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. All references patents, patent applications or other documents cited are herein incorporated by reference in their entirety.

Example 1

Mutational Spectrum of Primary Prostate Cancer

A. Materials and Methods
Description of Prostate Tumor Cohorts

Clinically localized primary prostate cancers were selected for exome- and transcriptome-sequencing from two cohorts: Weill Cornell Medical College (WCMC; New York, N.Y.) and Uropath (Perth, Australia), a commercial supplier of banked urological tissues. Patients were included only if they had not received previous treatment for prostate cancer, including radiation therapy, brachytherapy or hormone ablation therapy.

Tumors from the WCMC cohort were collected by the Institutional Biobank from patients undergoing radical prostatectomy by one surgeon for clinically localized prostate cancer. Patient-matched normal DNA was obtained from whole blood samples as described below for this cohort.

Tumors from the Uropath cohort were obtained from men undergoing radical prostatectomy for clinically localized prostate cancer across multiple medical centers in Western Australia. Radical prostatectomies were performed by one of 30 clinicians between 2000 and 2010. Samples from both cohorts were stored at −80° C. Paired normal DNA was derived and sequenced from benign prostate tissue. Normal DNA, was extracted from frozen tissue blocks with no histological evidence of neoplasia to minimize the possibility of contamination from tumor DNA.

For both cohorts, Hematoxylin and Eosin (H&E)-stained tissue sections were centrally reviewed to verify Gleason score and to determine the percentage of Gleason pattern 4 and 5 histology at the site selected for DNA extraction. To characterize the ethnic composition of the cohorts, high-density SNP array data was analyzed by principal component analysis in combination with data from cohorts of known ethnicity from the HapMap database (CEU, YRI, CHB/JPT; available through the International Haplotype Map (HapMap) Project website, National Center for Biotechnology Information (NCBI)). All but five individuals chosen for exome sequencing clustered with CEU HapMap samples, indicating that patients were predominantly Caucasian. Four samples showed mixed or undetermined ethnicity and one clustered clearly with CHB/JPT (Han Chinese in Beijing/Japanese in Tokyo) HapMap samples.

In addition to exome- and transcriptome-sequenced tumors, prostate tumor cohorts from University of Michigan (UM), University of Washington (UW) and University Hospital Zurich (UZH) were used for extension screening for SPOP mutation. Prostate samples from the UM cohort were obtained from the radical prostatectomy series at the University of Michigan and from the Rapid Autopsy Program (RUBIN (2000)), University of Michigan Prostate Cancer Specialized Program of Research Excellence Tissue Core (Ann Arbor, Mich.). Tumors from the UW cohort were obtained from the Rapid Autopsy Program, University of Washington and Fred Hutchison Cancer Research Center University (Seattle, Wash.). Samples from the UHZ cohort included a series of radical prostatectomy specimens, metastases, and benign prostatic hyperplasia samples. H&E-stained slides of all specimens were reevaluated by two experienced pathologists to identify representative areas. Tumor stage and Gleason score of the Zurich cohort were assigned according to the International Union Against Cancer and World Health Organization/International Society of Urological Pathology criteria.

All samples were collected with informed consent of the patients and prior approval of the institutional review boards (IRB) of respective institutions. Additionally, the sequencing and data release of all exome- and transcriptome-sequenced samples was reviewed and approved by local IRB.

DNA Extraction for Exome Sequencing

H&E slides were cut from all frozen tissue blocks and examined by a board-certified pathologist to select for high-density cancer foci with <10% stroma or other non-cancerous material to ensure high purity of cancer DNA. Biopsy cores were then taken from the corresponding frozen tissue block for DNA extraction. From each sample, 25-30 mg of tissue was homogenized using a tissuelyser for 20 seconds at 15 Hz. DNA was then isolated from the homogenate using the QIAamp mini kit (Qiagen) following the manufacturer's protocol. Samples were eluted in 150 µl AE elution buffer and quantified using Picogreen dsDNA Quantitation Reagent (Invitrogen, Carlsbad, Calif.). Samples were qualified on an agarose gel (E-Gel, Invitrogen) to assess structural integrity. All DNA samples were stored at −20° C.

Whole Exome Capture Library Construction

Whole exome hybrid capture libraries were constructed as described previously (FISHER (2011)) with minor modifications. Concentrations of tumor and normal DNA were measured using PicoGreen dsDNA Quantitation Reagent (Invitrogen, Carlsbad, Calif.). Genomic DNA (100 ng) was sheared to a range of 150-300 bp using the Covaris E220 instrument. DNA fragments were end-repaired, phosphorylated, adenylated at the 3' termini and ligated to Illumina sequencing adapters as described (FISHER (2011)), except that standard paired end adapters were replaced with forked adapters containing unique 8 base-pair index sequences (barcodes). Adapter-ligated DNA was then size-selected for lengths between 200-350 bp and subjected to exonic hybrid capture using SureSelect v2 Exome bait (Agilent) as described (FISHER (2011)). The targeted exome covered 44 Mb and comprised 98.2% of the CCDS database as of November 2010.

Library Quantitation and Sequencing

The number of properly adapter-ligated fragments in each library was quantified using quantitative PCR (qPCR) (Kapa Biosystems, Woburn Mass.) with specific probes for the ends of the adapters. Based on qPCR quantification, libraries were normalized to 2 nM and then denatured using 0.1 N NaOH. Barcoded whole exome libraries were pooled at equal molarities prior to sequencing with up to 93 samples per pool. Cluster amplification of denatured templates was performed according to manufacturer's protocol using V2 HiSeq Cluster Kits and V2 or V3 HiSeq Flowcells (Illumina, San Diego, Calif.). Paired-end sequencing (2×76 bp) was carried out on HiSeq Instruments, using V3 HiSeq Sequencing-by-Synthesis kits. The resulting data were analyzed with the current Illumina pipeline. Standard quality control metrics including error rates, % passing filter reads, and total Gb produced were used to characterize process performance prior to downstream analysis. The 8 bp adapter index of each sequence read was used to match the read to its corresponding sample in the downstream data aggregation pipeline.

Exome Sequence Data Processing

Two Broad Institute pipelines were used in succession to process and analyze exome sequencing data (BERGER (2011), STRANSKY (2011), CHAPMAN (2011)):

(1) The sequencing data processing pipeline "Picard", developed by the Sequencing Platform at the Broad Institute, starts with the reads and qualities produced by the Illumina software for all lanes and libraries and generates a BAM file (available through the SAMtools website on Sourceforge, particularly in the SAM1.pdf document) representing each tumor and normal sample. The final BAM file stores all reads with well-calibrated qualities together with their alignments to the genome (only for reads that were successfully aligned).

(2) The Broad Cancer Genome Analysis pipeline, also known as "Firehose", starts with the BAM files for the tumor and matched normal samples and orchestrates various analyses, including quality control, local realignment, mutation calling, small insertion and deletion identification, coverage calculations and others (see details below).

Several of the tools used in these pipelines were developed jointly by the Broad Institute Sequencing Platform, Medical and Population Genetics Program, and Cancer Program as part of the Genome Analysis Toolkit (GATK) (available through the Genome Analysis Toolkit web site of the Broad Institute). Additional details regarding these pipelines are provided in references (DEPRISTO (2011), MCKENNA (2010)).

a. Sequence data processing pipeline (Picard)

For each sample, a BAM file was generated from Illumina sequence reads using the Picard pipeline (available through the Picard pipeline website of the Broad Institute) as previously described (BERGER (2011), CHAPMAN (2011)). Briefly, Picard executes four steps: (1) alignment of sequence reads to the genome; (2) recalibration of base qualities based upon the quality score given by the Illumina software, the read-cycle, the lane, the tile and the identity of the base and the preceding base; (3) aggregation of lane-level and library-level data into a single BAM file per sample; and (4) marking of artifactual duplicate read pairs. These steps were performed as in (CHAPMAN (2011)), with the following modification: sequence reads were aligned to the NCBI Human Reference Genome GRCh37 using the Burrows-Wheeler Aligner (BWA, website on Sourceforge) (LI (2009)).

b. Cancer genome analysis pipeline (Firehose)

Firehose, a cancer genome analysis pipeline infrastructure developed at the Broad institute, was used to analyze exome sequence data. The Firehose interface manages input files, output files and a variety of analysis tools. Firehose submits input files and parameters to GenePattern (REICH (2006)), which serves as the execution engine of Firehose and runs the specified modules or analyses. The analyses described below were performed as in (BERGER (2011), STRANSKY (2011), CHAPMAN (2011)), with modifications where indicated.

Quality Control

The quality control modules in Firehose were used to ensure that each tumor and normal file corresponded to the correct individual, and that no mix-ups had occurred between tumor and normal data for a given individual. Genotypes from Affymetrix SNP 6.0 arrays and from tumor and normal sequence data for each individual were compared to ensure that all data corresponded to the correct patient. Genotypes from SNP arrays were also used to monitor for low levels of cross-contamination between samples from different individuals in sequencing data via the ContEst algorithm (CIBULSKIS (2011)).

Local Realignment

Sequence reads corresponding to genomic regions that may harbor small insertions or deletions (indels) were realigned to improve detection of indels and to decrease the number of false positive single nucleotide variant calls caused by misaligned reads, particularly at the 3' end (DEPRISTO (2011)). To improve the efficiency of this step, a joint local-realignment of tumor and normal sequences from each individual (termed "co-cleaning") was performed. Briefly, all sites potentially harboring small insertions or deletions in either the tumor or the matched normal were realigned in both samples.

Identification of Somatic Single Nucleotide Variants (SS-NVs)

The MuTect algorithm from the Broad Institute Genome Analysis Toolkit was used to identify SSNVs (CHAPMAN (2011), C. I. G. A. R. Network (2011)) with one modification: the lowest allelic fraction at which SSNVs could be detected on a per-sample basis was determined using estimates of cross-contamination from the ContEst pipeline (CIBULSKIS (2011)). MuTect identifies candidate SSNVs by performing a statistical analysis of the bases and their qualities in the tumor and normal BAMs at the genomic locus under examination. Mutations were sought in the neighborhood of the targeted exons, where the majority of reads are located. For every analyzed base, at least 14 reads in the tumor and 8 in the normal were required to consider a base sufficiently covered for confident identification of SSNVs. In brief, the SSNV detection consists of three steps:

(1) Preprocessing of the aligned reads in the tumor and normal sequencing data. This step ignores reads with too many mismatches or very low quality scores since they are likely to introduce artifacts.

(2) A statistical analysis that identifies sites that are likely to carry somatic mutations with high confidence. The statistical analysis predicts a somatic mutation by using two Bayesian classifiers. The first classifier aims to detect whether the tumor is non-reference at a given site. For those sites that are found to be non-reference, the second classifier makes sure that the normal does not carry the variant allele in order to exclude germline events. The classification is performed by calculating an LOD score (log odds) and comparing it to a cutoff determined by the log ratio of prior probabilities of the considered events. For a tumor, the calculation is:

$$LOD_T = \log_{10}\left(\frac{P(\text{observed data in tumor}|\text{site is mutated})}{P(\text{observed data in tumor}|\text{site is reference})}\right)$$

In the corresponding normal, the calculation is:

$$LOD_N = \log_{10}\left(\frac{P(\text{observed data in normal}|\text{site is reference})}{P(\text{observed data in normal}|\text{site is mutated})}\right)$$

Thresholds were chosen for each statistic such that the false positive rate was sufficiently low.

(3) Post-processing of candidate somatic mutations to eliminate artifacts of next-generation sequencing, short read alignment and hybrid capture. For example, sequence context can cause hallucinated alternate alleles but often only in a single direction. Therefore, testing is performed to confirm that the alternate alleles supporting the mutations are observed in both directions.

Mutation calls for significantly mutated genes were reviewed manually by examination of the corresponding BAM files in the Integrative Genomics Viewer (IGV) (ROBINSON (2011)).

Identification of Somatic Small Insertions and Deletions (Indels)

Indels were detected in two steps (C. I. G. A. R. Network (2011)). First, high sensitivity calls of putative indels were made with thresholds set for minimum coverage and minimum fraction of indel-supporting reads at the locus. Second, the calls were filtered based on local alignment statistics around the putative event, including the average number of additional mismatches per indel-supporting read, average mismatch rate and base quality in a small NQS window around the indel. Indels called in significantly mutated genes and other cancer-associated genes were manually reviewed by inspecting the tumor and normal BAM files in IGV.

Determination of Mutation Rates

Rates of base mutations per Mb were calculated using the mutations detected (SSNVs and indels) and coverage statistics. Mutations were partitioned into categories based on their relative frequency such as (1) a C in a CpG dinucleotide mutated to T (CpG C to T transition), (2) all other Cs mutated to T (non-CpG C to T transition), (3) mutation of any C to G or A and (4) mutation of A to any other base. Disruptive mutations such as frame-shift indels and nonsense mutations were also considered separately.

Because mutations may accumulate in benign-appearing tissue, it was determined if the use of benign prostate as the source of normal DNA affected the ability to distinguish somatic alterations from germline events. Tumors with matched normal prostate (n=89) did not show different rates of mutation from tumors with blood matched normal (n=22), indicating that the use of normal prostate did not prevent the detection of tumor-specific mutations.

The allelic fraction (AF) values of mutations were used to characterize the relative purity of cancer DNA in each tumor (SOM). AF is the number of reads supporting a mutant allele divided by the total number of reads covering the mutated site. The relative purity of cancer DNA as assessed by AF did not vary by pathological stage or Gleason score.

B. Results

The mutational spectrum of primary prostate cancer was determined by exome capture and paired-end sequencing performed on genomic DNA from 112 primary prostate adenocarcinomas and matched normal samples. Treatment-naïve tumors were selected that spanned clinically relevant grades and stages (Table 1). The targeted exome included 98.2% of genes in the Consensus CDS database (CCDS, available through the National Center for Biotechnology Information (NCBI) web site). A mean coverage depth of 118× per sample was achieved, with 89.2% of targets covered at ≥20× depth. A single highly-mutated tumor (PR-00-1165) was excluded from subsequent analyses, except where otherwise indicated, leaving 111 pairs. Tumor and normal DNA were also analyzed by Affymetrix SNP 6.0 arrays to detect somatic copy number alterations. In addition, transcriptome sequencing ("RNA-seq") was performed on 22 exome-sequenced tumors and 41 independent samples All but four of the 112 exome-sequenced tumors, plus an additional 61 tumors, were analyzed for copy number alteration by high-density SNP array (169 total) (FIG. 1).

This analysis identified 5,764 somatic mutations that were present in tumor DNA but absent in peripheral blood or non-cancerous prostate. Of these, 997 variants occurred in a single tumor that harbored a frame-shift mutation of the mismatch-repair gene MSH6. After excluding this highly-mutated sample, the remaining tumors harbored a median of 10 silent and 30 non-silent mutations (range 10 to 105 total mutations) or ~1.4 per Mb covered. Analysis of 229 non-silent mutations by mass-spectrometric genotyping validated 95.6% of variants with allelic fraction ≥0.2 (C.I. 92-98%). The mutation rate of this cohort exceeded that of seven published prostate tumor genomes (0.9 mutations per Mb) (BERGER (2011)), perhaps because the increased exome sequence coverage improved detection of variants present at lower allelic fractions. Interestingly, the base mutation rate showed no correlation with Gleason score (a histological measure of disease risk), indicating that mutational burden does not track uniformly with disease aggressiveness. Mutation rates were higher in pT3 tumors relative to pT2 tumors (P=0.001) but did not vary by Gleason pattern or TMPRSS2-ERG fusion status. Both the number and proportion of CpG to T mutations is increased in TMPRSS2-ERG fusion positive tumors (P=0.0002).

Two-tailed p values were from the Mann Whitney test or Kruskal-Wallis test (Gleason score groups). Statistical analysis was performed using GraphPad Prism.

TABLE 1

Characteristics of Exome-sequenced Primary Prostate Cancers

| Characteristic | Whole exome-sequenced tumors | |
|---|---|---|
| Age, years | | |
| Median (range) | 63 | (34-77) |
| Pre-operative Serum PSA (ng/μL) | | |
| Median (range) | 7.8 | (2.7-31.5) |
| Pathologic Stage, N % | | |
| Stage pT2 Total | 44 | 39% |
| Stage pT2a | 4 | 4% |
| Stage pT2b | 1 | 1% |
| Stage pT2c | 39 | 35% |
| Stage pT3 Total | 68 | 61% |
| Stage pT3a | 49 | 44% |
| Stage pT3b | 18 | 16% |
| Stage pT3c | 1 | 1% |
| Gleason Pattern (major + minor), N %* | | |
| Gleason 3 + 3 | 13 | 12% |
| Gleason 3 + 4 | 58 | 52% |
| Gleason 4 + 3 | 29 | 26% |
| Gleason 4 + 4 | 8 | 7% |
| Gleason 4 + 5 | 4 | 4% |
| Percentage of Gleason Pattern 4 and 5, N %* | | |
| 0-19% | 40 | 36% |
| 20-39% | 23 | 12% |
| 40-59% | 5 | 5% |
| 60-79% | 12 | 11% |
| 80-100% | 29 | 26% |
| TMPRSS2-ERG Fusion Status, N %[†] | | |
| Fusion-negative | 53 | 48% |
| Fusion with interstitial deletion | 34 | 31% |
| Fusion without interstitial deletion | 24 | 22% |

*Gleason scores based on review of hematoxylin and eosin slides from site of tumor chosen for DNA extraction and sequencing
[†]TMPRSS2-ERG fusion status assessed by FISH.

Example 2

SPOP is the Most Frequently Mutated Gene In Prostate Cancer

A. Materials and Methods
Identification of Significantly Mutated Genes

The MutSig algorithm from the Broad Institute was applied to identify genes that were significantly enriched for mutations as previously described (BERGER (2011), CHAPMAN (2011), C. I. G. A. R. Network (2011)) with two modifications. First, at most one mutation per gene was considered from each sample. Second, the observed number of silent mutations was used as a guide to the local background mutation rate. Briefly, MutSig identifies genes that harbor more mutations than expected by chance given sequence context and genic territory. Because certain base contexts exhibit increased mutation rates, such as cytosine in CpG dinucleotides, the context-specific mutation rates are considered for each class of mutation listed under "Determination of mutation rates" (Example 1.A above). Bases were considered sufficiently covered for calling substitutions if covered by at least 14 reads in the tumor and 8 reads in the normal. For each gene, the probability of detecting the observed constellation of mutations or a more extreme one was calculated, given the background mutation rates calculated across the dataset. This was done by convoluting a set of binomial distributions, as described previously (GETZ (2007)). This p-value is then adjusted for multiple hypotheses according to the Benjamini-Hochberg procedure for controlling False Discovery Rate (FDR) (BENJAMINI, (1995)) to obtain a q-value. The hyper-mutated sample was excluded from this analysis.

Identification of Significantly Mutated Gene Sets

MutSig was used to determine whether particular gene sets were enriched for mutations (BERGER (2011), CHAPMAN (2011)). The list of canonical pathways used in Gene Set Enrichment Analysis (GSEA) was downloaded and 616 gene sets corresponding to known pathways or gene families were analyzed. For each gene set, the number of mutations occurring in any component gene was tabulated as well as the total number of covered bases in all genes in the gene set. A p-value was calculated for each gene set as for each gene, then a q-value was computed to account for the list of 616 hypotheses. The hyper-mutated sample was excluded from this analysis.

Mutation Annotation

Point mutations and indels identified were annotated using which integrates information from publicly available databases. In brief, a local database of annotations compiled from multiple public resources was used to map genomic variants to specific genes, transcripts, and other relevant features. The set of 73,671 reference transcripts used were derived from transcripts from the UCSC Genome Browser's UCSC Genes track (FUJITA (2011)) and microRNAs from miRBase release 15 (KOZOMARA (2011)) as provided in the TCGA General Annotation Files 1.0 library (available through the National Cancer Institute (NCI) Wiki website). Variants were also annotated with data from the following resources: dbSNP build 132 (SHERRY (2001)), UCSC Genome Browser's ORegAnno track (GRIFFITH (2008)), UniProt release 2011_03 (CONSORTIUM (2011)) and COSMIC v51 (FORBES (2011)).

Validation of Selected Mutations by Mass Spectrometric Genotyping

To validate detected mutations with an orthogonal genotyping method, 240 non-silent mutations (231 SSNVs and 9 indels) across 48 T/N pairs were assayed by mass spectrometric genotyping using the iPLEX platform (Sequenom, San Diego, Calif.). A selection of 74 mutations in significantly-mutated genes or gene sets with a q-value <0.1 and mutations reported in COSMIC were targeted for genotyping. The remaining 166 non-silent mutations were chosen at random. Because the rate of validation using this technology falls significantly when the mutant allele is present at low allelic fraction (BERGER (2011), STRANSKY (2011)), to the extent possible, only mutations with AF≥0.2 (i.e., where 20% of sequence reads from the tumor contain the mutation) were validated.

Of the 240 assays attempted, 228 gave successful genotype calls and 218 somatic mutations were confirmed. All events called in the tumor were absent from the corresponding normal. Hence, the overall accuracy for mutation calling was 95.6% (CI: 92%-98%; Clopper-Pearson 95% confidence interval), in close agreement with previous studies (BERGER (2011), STRANSKY (2011), CHAPMAN (2011)).

High-Density SNP Array Analysis and Detection of Somatic Copy Number Alteration

Genomic DNA from tumor and paired blood samples was processed using Affymetrix Genome-Wide Human SNP Array 6.0 (Affymetrix, Inc.) according to manufacturer's protocols. The DNA was digested with NspI and StyI enzymes (New England Biolabs), ligated to the respective Affymetrix adapters using T4 DNA ligase (New England Biolabs), amplified (Clontech), purified using magnetic beads (Agencourt), labeled, fragmented, and hybridized to the arrays. Following hybridization, the arrays were washed and stained with streptavidin-phycoerythrin (Invitrogen). Following array scanning, data preprocessing was performed using Affymetrix Power Tools. Copy number data was evaluated after segmenting the log 2 ratios between tumor and paired normal levels on a sample basis. Quality control, data integrity, segmentation and copy number analysis were performed as previously described (DEMICHELIS (2009)) with one additional step aimed at diminishing the number of recurrent lesions possibly caused by germline signal: the same detection pipeline was applied on the normal DNA samples alone. All peaks detected in both analyses were excluded from the recurrent somatic copy number aberration list. Cleared lesions with q-value <0.1 were retained for association analysis with gene mutation status. Two-tail Fisher Exact Test was applied for all association tests. Copy number aberration images were generated with Integrated Genomics Viewer (ROBINSON (2011)).

Assessment of Tumor Purity

Because prostate tumors may contain significant amounts of admixed stroma, the purity of the cancer DNA was evaluated to determine whether it limited the ability to detect mutations. Tumor purity was assessed by considering the allelic fractions (AF) of mutations detected in each tumor, defined as the number of mutation-supporting reads divided by the total number of reads mapping to a mutated locus. Allelic fraction can be influenced by several factors in addition to tumor purity, including copy number alterations at mutated sites and the presence of subclones within a tumor. Therefore, the AF data was used to assess purity in two ways. First, the maximum mutant AF value across all mutations in each tumor was considered after removing the top fifth percentile of AF values in order to exclude outliers with elevated AF due to copy number alterations or stochastic effects. Second, the median AF for all mutations across a tumor was considered.

Both the maximum and median AF values correlated only slightly with the number of mutations detected, suggesting that tumor purity was not a systematic barrier to identifying mutations. Comparing mutation rates across subgroups of tumors (e.g. Stage pT2 versus pT3), showed that no systematic differences in tumor purity existed between subgroups. To this end, comparing mutant and maximum AF for each subgroup, identified no differences.

RNA Extraction, RNA-seq Sample Prep and Sequencing

RNA was extracted from the frozen cancer tissue using TRIzol (Invitrogen) according to the manufacturer's protocol. Total RNA was prepared in accordance with Illumina's sample preparation protocol for PE sequencing of mRNA as previously described (PFLUEGER (2011)). In brief, 5-10 µg of total RNA was fragmented by heat between 2 and 3 min based on the desired insert size, reverse-transcribed using Superscript II (Invitrogen), and transformed to double-stranded cDNA. To improve paired-end (PE) RNA-seq data quality, an additional gel-based size selection step was performed after cDNA double-strand synthesis and before the ligation of the PE adapters. This was postulated by Quail et al. (QUAIL (2008)) as a means to reduce the inclusion of artifactual chimeric transcripts that are composed of two cDNA fragments into the sequencing library. T4 ligase (Enzymatics Inc.) was used to improve the efficiency of adapter ligation. Over the course of the study, the library size range increased from 250 bp to 450 bp. The gel dissolutions of all gel-based purification steps were conducted at room temperature under slight agitation as described by Quail et al. (QUAIL (2008)). After the enrichment of cDNA template by PCR, the concentrations and the sizes of the libraries were measured using a Qubit fluorometer (Invitrogen) and DNA 1000 kit (Agilent Technologies) on an Agilent 2100 Bioanalyzer, respectively. PE RNA-seq was performed with the Genome Analyzer II (Illumina) increasing the read size of the PE reads from 36 to 54 bp over the course of the study. Additionally, Illumina introduced improved sequencing reagents and upgraded imaging software over time to increase data quality and sequencing coverage.

Processing of RNA-seq Data

PE reads were aligned to the human genome (hg18) using ELAND, part of the standard software suite from Illumina, as previously described (PFLUEGER (2011)). Data were visualized using the Integrated Genomics Viewer (ROBINSON (2011)), and candidate mutations were identified in SPOP coding regions.

DNA Extraction and SPOP Genotyping

DNA was extracted using phenol-chloroform and purified by ethanol precipitation method as previously described (BERGER (2011)). Direct Sanger sequencing of putative SPOP somatic mutations in all tumor-blood pairs was performed by standard methods following PCR amplification using specific primers. Sequences of the primers used for amplifying and sequencing SPOP are given in Table 2.

TABLE 2

Primer Sequences

| | sense (5'--->3') | antisense (5'--->3') |
|---|---|---|
| Amplification | | |
| SPOP Exons 6 and 7 | TTCTATGGGGCCTGCATTT (SEQ ID NO. 1) | CTCCACTTGGGGCTTTTTCT (SEQ ID NO. 2) |
| Sequencing | | |
| SPOP Exon 6 | TTTTCTATCTGTTTTGGACAGG (SEQ ID NO. 3) | CAAAGCCACAACTTGTCAGTG (SEQ ID NO. 4) |

TABLE 2-continued

Primer Sequences

| | sense (5'-->3') | antisense (5'-->3') |
|---|---|---|
| Exon 7 | TTTGCGAGTAAACCCCAAAG (SEQ ID NO. 5) | CTCATCAGATCTGGGAACTGC (SEQ ID NO. 6) |
| qPCR | | |
| SPOP | CTTCTGCGAGGTGAGTGTTG (SEQ ID NO. 7) | TCCCACAGTCCTCCTAACTCA (SEQ ID NO. 8) |
| GAPDH | TGCACCACCAACTGCTTAGC (SEQ ID NO. 9) | GGCATGGACTGTGGTCATGAG (SEQ ID NO. 10) |
| PTCH1 | ACAAACTCCTGGTGCAAACC (SEQ ID NO. 11) | AAGCGCTGGGATTAATGATG (SEQ ID NO. 12) |
| GLI1 | ATCAGGGAGGAAAGCAGACT (SEQ ID NO. 13) | TGTCTGTATTGGCTGCACTC (SEQ ID NO. 14) |

B. Results

Figure 7:
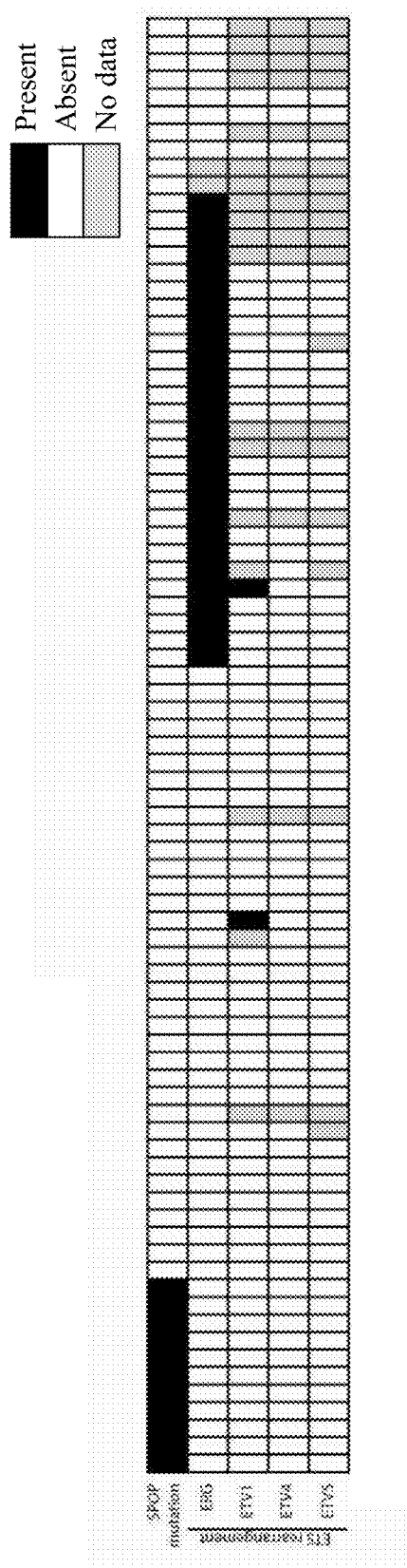
FIG. 7. Tumors with SPOP mutation lack ETS rearrangements. Heatmap showing SPOP mutation status and rearrangement status of ETS genes in WCMC cohort.

The data were analyzed to find genes that harbored more non-synonymous mutations than expected by chance given gene size, sequence context and the frequency of mutations for each tumor (FIG. 7). Substitutions in significantly mutated genes were documented at the transcript and protein level for exome-sequenced samples. Twelve genes, identified in FIG. 2, were enriched for mutations at q-value <0.1, the majority of which are highly expressed at the transcript level in prostate tumors. The identification of PIK3CA, TP53 and PTEN confirmed that this approach detected alterations known to promote tumorigenesis in prostate cancer and other malignancies. Evidence was found for enrichment of mutations in the PTEN pathway, cell cycle regulatory machinery, and other gene sets (TAYLOR (2010)).

Figure 2:
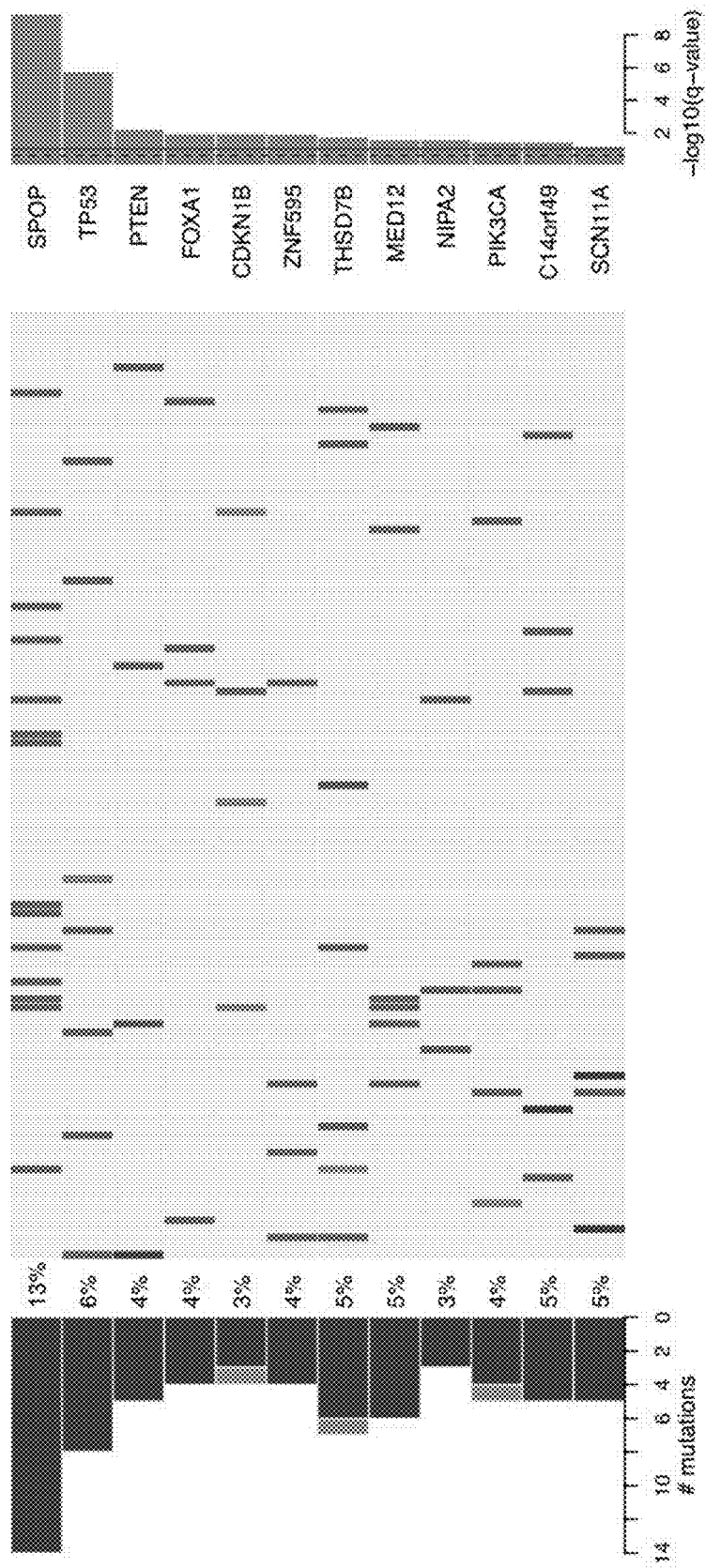

By next-generation sequencing, the most frequently mutated gene was SPOP (13% of cases; FIG. 2, left panel), which encodes the substrate-binding subunit of a Cullin-based E3 ubiquitin ligase (NAGAI (1997), ZHUANG (2009)). The observed SPOP mutations and their chromosomal locations are shown in Table 3. Although isolated SPOP mutations have been reported in prostate cancer (BERGER (2011)), this gene has not previously been found significantly mutated in any malignancy. Several additional genes not previously known to undergo somatic alteration in prostate cancer were enriched for mutations, including FOXA1, MED12, THSD7B, SCN11A and ZNF595. The p27$^{Kip1}$ gene CDKN1B was somatically mutated in three samples and deleted in sixteen others. p27$^{Kip1}$ constrains prostate tumor growth in mice (MAJUMDER (2008)) and harbors a germline prostate cancer risk allele (KIBEL (2003)), but somatic substitutions have not previously been observed in this cell cycle regulatory protein. Infrequent mutations were also detected in multiple proto-oncogenes, tumor suppressors, and chromatin-modifying enzymes (FIG. 3).

Figure 3:
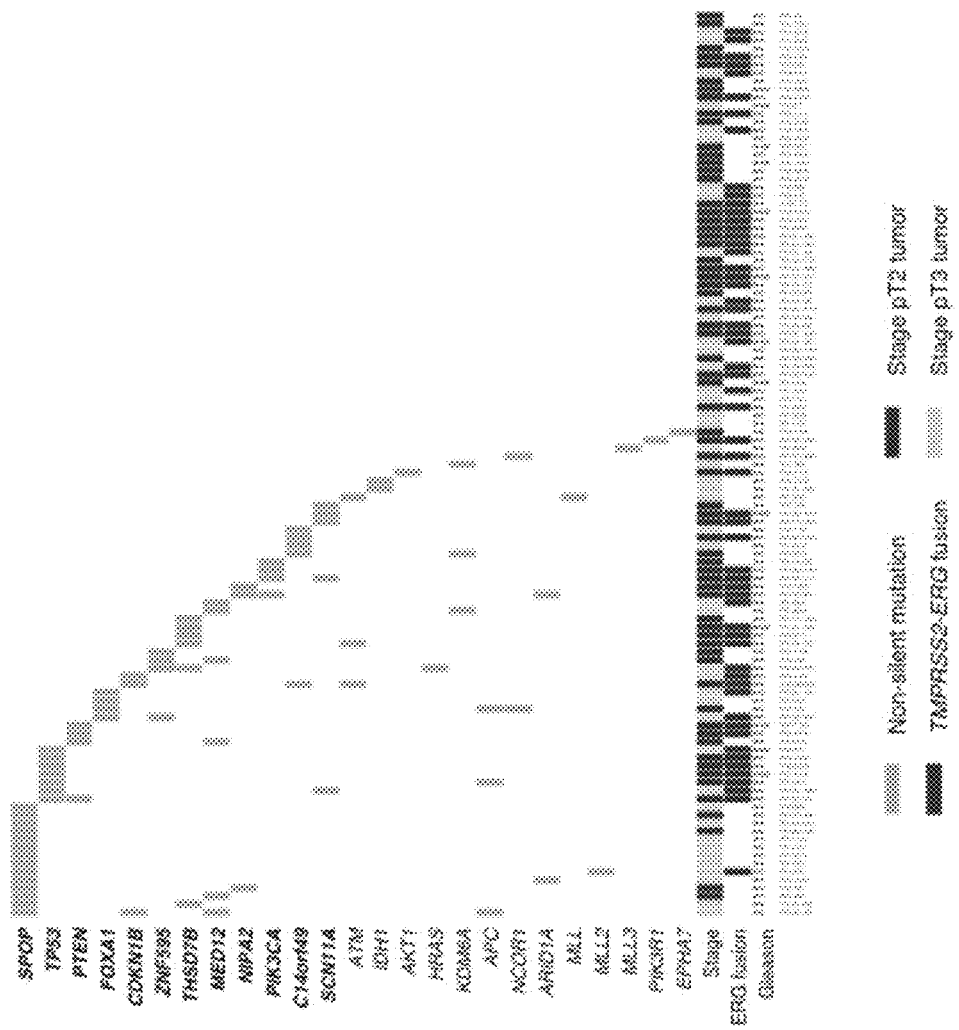
FIG. 3. Mutations in significantly-mutated genes and selected cancer-associated genes. Boxes across from gene symbol represent non-synonymous mutations in significantly-mutated genes (listed in bold font) and several additional genes that are frequently mutated in other cancer types. Each column represents an exome-sequenced tumor-normal pair. Pathological stage and TMPRSS2-ERG fusion status are indicated in the bottom two rows.

Multiple genes with established roles in other cancers were mutated at low frequency, including IDH1, AKT1 and HRAS (FIG. 3). An analysis of predicted "damaging" mutations (nonsense substitutions, frame-shift indels and splice site alterations) in genes expressed in prostate tumors identified mutations in APC, PIK3R1 and EPHA7 (FIG. 3). In addition, several chromatin-modifying enzymes harbored low-frequency damaging mutations, including MLL1, MLL2, MLL3, ARID1A, NCOR1 and the histone demethylase gene KDM6A (UTX). Two KDM6A mutations involved residues situated within the catalytic Jumonji domain (I1209 and G1212), while a third introduced a frame-shift deletion directly N-terminal to this region. These findings underscore the emerging importance of chromatin-modifying genes in prostate cancer (GAO (2010)). Notably, AR was not mutated in any primary tumor analyzed, consistent with prior studies suggesting that mutations in this gene are restricted to metastatic or castration-resistant disease (LINJA (2004), TAYLOR (2010)).

Figure 4:
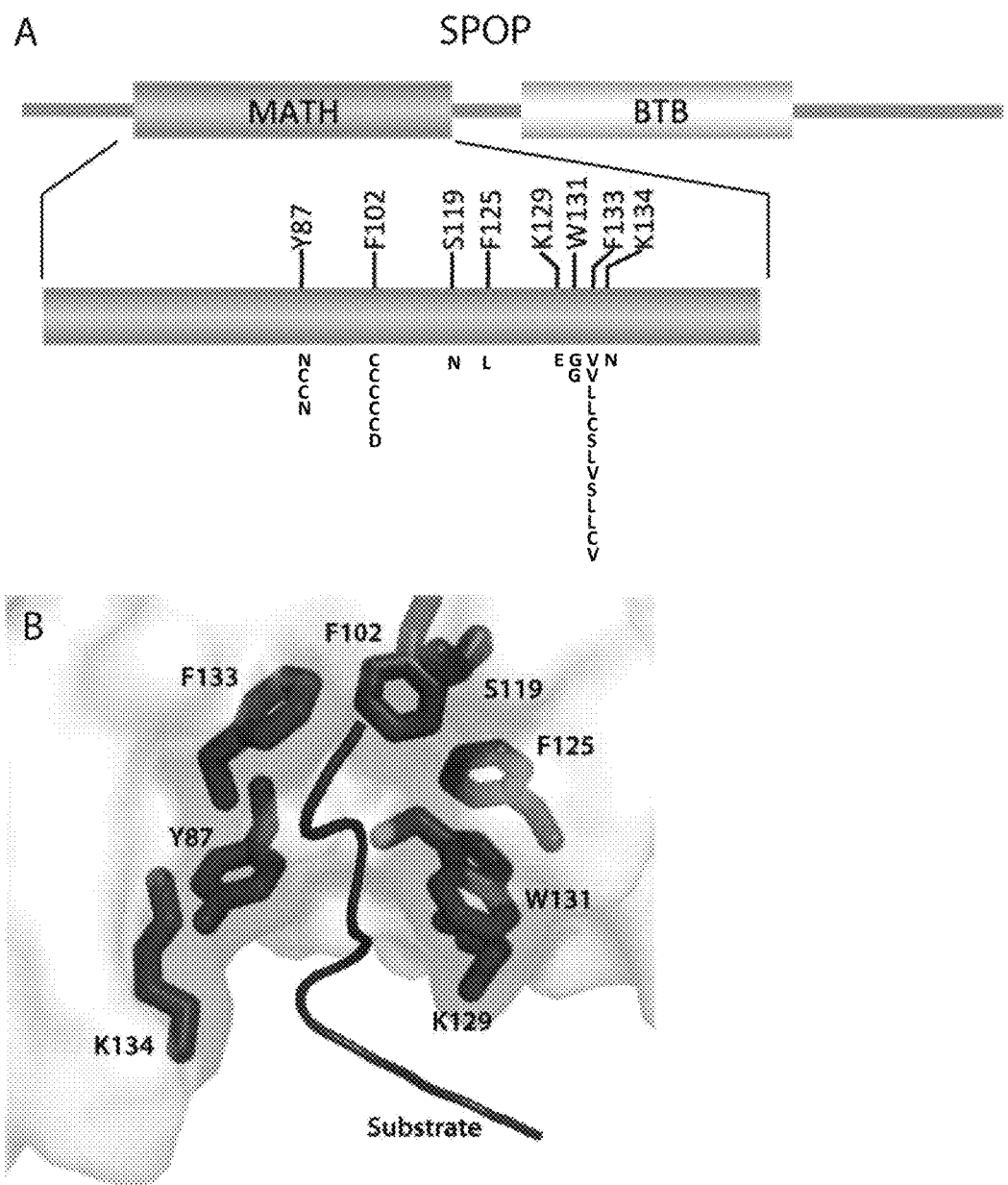
FIG. 4A-B. Structural and functional studies of recurrent SPOP mutations in prostate cancer. (A) Positional distribution of somatic mutations in SPOP. (B) Mutated residues in the crystal structure of the SPOP MATH domain bound to substrate (PDB 3IVV). Meprin and TRAF Homology (MATH) and Bric-a-brac, Tramtrack, Broad-complex (BTB) domains are depicted in A.

Although SPOP mutations were originally reported in genomic studies of prostate cancer (Table 4) (BERGER (2011), KAN (2010)), their prevalence and functional relevance remained unknown. Accordingly, the SPOP gene was sequenced in multiple additional cohorts comprising over 400 primary tumors and metastases from the US and Europe. Using RNA-seq, whole exome sequencing and Sanger sequencing of tumor and matched germline DNA, recurrent heterozygous SPOP substitutions were identified in 6-13% of primary prostate adenocarcinomas. No mutations were identified in 36 benign prostate tissue samples, prostate stroma, or common prostate cell lines. SPOP mutations were also found in 5 of 41 patients with metastatic disease (14.5%) (FIG. 4A, Table 5). Thus, SPOP mutations occur at a 6 to 15% frequency across localized and advanced prostate tumors.

All SPOP mutations affected conserved residues in the structurally-defined substrate binding cleft in the MATH domain of SPOP (FIG. 4B) (ZHUANG (2009)). The MATH residues mutated in prostate cancer include Y87, F102, S119, F125, K129, W131, F133 and K134. Several recurrently mutated residues exert key substrate-interacting roles; moreover, mutation of Y87, W131, and F133 disrupts substrate binding in vitro (ZHUANG (2009)). These results suggest that prostate cancer SPOP mutations are biologically significant.

TABLE 3

SPOP Mutations

| Gene symbol (Transcript) | Patient | Genomic coordinates (hg19) | Variant type | Codon change | Protein change | Median RNA | Mean RNA | RNA CV | RNA Percentile |
|---|---|---|---|---|---|---|---|---|---|
| SPOP (uc010dbk.2) | P04-2599 | g.chr17: 47696425A > G | Missense | c.(397-399)TTC > TCC | p.F133S | 3.88 | 3.78 | 0.13 | 88% |
| | P07-684 | g.chr17: 47696448A > T | Missense | c.(373-375)TTT > TTA | p.F125L | | | | |
| | P07-837 | g.chr17: 47696424G > C | Missense | c.(397-399)TTC > TTG | p.F133L | | | | |
| | P09-649 | g.chr17: 47696467C > T | Missense | c.(355-357)AGT > AAT | p.S119N | | | | |
| | PR-00-160 | g.chr17: 47696421C > G | Missense | c.(400-402)AAG > AAC | p.K134N | | | | |
| | PR-01-2492 | g.chr17: 47696425A > C | Missense | c.(397-399)TTC > TGC | p.F133C | | | | |
| | PR-04-3222 | g.chr17: 47696424G > T | Missense | c.(397-399)TTC > TTA | p.F133L | | | | |
| | PR-05-839 | g.chr17: 47696689A > T | Missense | c.(259-261)TAC > AAC | p.Y87N | | | | |
| | PR-09-5245 | g.chr17: 47696432A > C | Missense | c.(391-393)TGG > GGG | p.W131G | | | | |
| | PR-2661 | g.chr17: 47696426A > C | Missense | c.(397-399)TTC > GTC | p.F133V | | | | |
| | PR-2740 | g.chr17: 47696424G > T | Missense | c.(397-399)TTC > TTA | p.F133L | | | | |
| | PR-2761 | g.chr17: 47696425A > G | Missense | c.(397-399)TTC > TCC | p.F133S | | | | |
| | PR-2915 | g.chr17: 47696426A > C | Missense | c.(397-399)TTC > GTC | p.F133V | | | | |
| | PR-3051 | g.chr17: 47696438T > C | Missense | c.(385-387)AAA > GAA | p.K129E | | | | |

The SPOP annotation is based on the UCSC Genome Browser identifier listed in the left column beneath the SPOP gene symbol. The right-most four columns summarize expression data for the SPOP gene from the panel of 63 tumors profiled by transcriptome sequencing;
"RNA" refers to the $\log_{10}(RPKM + 1)$ value for each transcript.
CV, coefficient of variation.

TABLE 4

Systematic Sequencing Studies Including SPOP

| Cancer type | Samples (N) | SPOP mutations | Ref | Approach |
|---|---|---|---|---|
| Prostate | 7 | 2: F102C, F133V | (14) | Paired-end whole-genome sequencing |
| Prostate | 58 | 2: F125V, F133V | (30) | Mismatch repair detection (MRD) |
| Lung | 134 | 2: N169S, L190F | (30) | Mismatch repair detection (MRD) |
| Ovarian | 316 | 1: E249* | (45) | Whole exome sequencing |
| Ovarian | 8 | 1: E47K | (83) | Whole exome sequencing |
| Ovarian | 58 | None | (30) | Mismatch repair detection (MRD) |
| HNSCC | 76 | None | (38) | Whole exome and paired-end whole-genome sequencing |
| RCC | 101 | None | (84) | PCR-based exon resequencing |
| RCC | 7 | None | (85) | Whole exome sequencing |
| Pancreatic | 8 | None | (30) | Mismatch repair detection (MRD) |
| Pancreatic | 24 | None | (86) | Whole exome sequencing |
| Breast | 183 | None | (30) | Mismatch repair detection (MRD) |
| Breast | 11 | None | (87) | Whole exome sequencing |
| Breast | 24 | None | (88) | Paired-end whole-genome sequencing |
| Medulloblastoma | 22 | None | (77) | Whole exome sequencing |
| GBM | 22 | None | (66) | Whole exome sequencing |
| Colorectal | 11 | None | (87) | Whole exome sequencing |
| AML | 1 | None | (89) | Single-end whole-genome sequencing |
| AML | 1 | None | (90) | Paired-end whole-genome sequencing |
| Melanoma | 1 | None | (91) | Paired-end whole-genome sequencing |
| SCLC | 1 | None | (92) | Paired-end whole-genome sequencing |

TABLE 5

SPOP mutations in multiple cohorts

| Cohort | SPOP mutation prevalence | Technology | Mutated residues |
|---|---|---|---|
| WCMC | 13.3% (11/83) | WES, RNA-seq, Sanger | Y87N, Y87C, F102C, K129E, F133V, F133S, F133L, F133C |
| Uropath | 10.1% (9/89) | WES | Y87N, S119N, F125L, W131G, F133S, F133L, F133C, K134N |
| UM | 6.1% (3/49) | RNA-seq | F102C, F133L, F133V |
| UHZ | 8.3% (16/193) | Sanger | Y87N, F102C, F102S, W131C, F133V, F133L |
| UW | 14.5% (6/39) | Sanger | F102C, F102D, W131G, F133V |

Example 3

In Vitro Assessment of SPOP Tumorigenic Phenotype

A. Materials and Methods
SPOP wt and Mutant Plasmids

Wild-type SPOP was obtained from Origene (Rockville, Md.) with C-terminal myc and FLAG tags in a mammalian expression vector. SPOP-F133V was created by using the QuikChange II site-directed mutagenesis kit (Agilent). All plasmids were confirmed with Sanger sequencing, and protein expression was confirmed with Western blot using antibodies to SPOP, myc, and FLAG.

Cell Culture and Transfection

The human prostate cancer cell lines 22Rv1, and DU145 and the benign prostate cell line RWPE were obtained from the American Type Culture Collection (Manassas, Va.). The 22Rv1 and DU145 cells were maintained in RPMI 1640 (Invitrogen) supplemented with 10% fetal bovine serum (FBS) and penicillin/streptomycin. RWPE cells were maintained in Keratinocyte-SFM (Invitrogen) supplemented with human recombinant Epidermal Growth Factor and Bovine Pituitary Extract (BPE).

For siRNA transfection, RWPE ($2.5 \times 10^5$ per well), 22Rv1 ($4 \times 10^5$ per well), and DU145 ($2 \times 10^5$ per well), cells were seeded on 6-well tissue culture plates. The next day, cells were transfected with 100 nM SPOP or nontargeting (control) siRNAs (ON-TARGET plus; Thermo Scientific) using Dharmfect 2 reagent (Invitrogen) according to the manufacturer's instructions. For plasmid transfection, DU145 ($4 \times 10^5$ per well), cells were seeded on 6-well tissue culture plates. The next day, cells were transfected with 4 µg of pCMV6-WT SPOP or pCMV-SPOP-F133V using Lipofectamine 2000 (Invitrogen) according to the manufacturer's instructions.

Cell Viability and Proliferation Assays

22Rv1 ($2 \times 10^3$ per well) and DU145 ($1 \times 10^3$ per well) cells transfected with control or SPOP siRNA or SPOP plasmids were seeded in 96-well tissue culture plates. Cell viability and growth was determined by performing WST-1 assay (Roche) reading absorbance at 450 nm according to the manufacturer's instructions. Values from three wells were obtained for each treatment and time point. Results are representative of three independent experiments.

Quantitative RT-PCR

RNA was extracted using the TRIzol reagent (Invitrogen), subjected to DNase treatment (DNA-free kit; Applied Biosystems) according to the manufacturer's instructions, and used in quantitative RT-PCR. Quantitative RT-PCR was performed using the ABI 7500 Real-Time PCR System (Applied Biosystems) following the manufacturer's RNA-to-CT 1-step protocol. Each target was run in triplicate, and expression levels relative to the housekeeping gene GAPDH were determined on the basis of the comparative threshold cycle CT method ($2^{-\Delta\Delta CT}$). The primer sequences used in these experiments are given in Table 2. All experiments were run in triplicate; results are representative of three independent experiments.

Invasion Assays

For invasion assays, $7.5 \times 10^4$ 22Rv1 and $5 \times 10^4$ DU145 cells transfected with control or SPOP siRNA or SPOP plasmids were resuspended in 0.5 mL of RPMI-1640 medium containing 1% FBS and placed into the top chamber of Matrigel-coated 8-µm Transwell inserts (BD Falcon). The bottom wells contained RPMI supplemented with 5-10% FBS. After 24 h (DU145) or 48 h (22Rv1), the filters were fixed and stained with Crystal Violet 0.5% for 30 min, and cells on the upper surface of the filters were removed with a cotton swab. Migrated cells were quantified by counting the numbers of cells that penetrated the membrane in four microscopic fields (at 20× objective magnification) per filter. All experiments were run in triplicate; results are representative of three independent experiments.

B. Results

To examine the biological significance of SPOP mutation, the consequences of mutant SPOP protein expression or SPOP knockdown on tumorigenic phenotypes in vitro was determined. Expression of SPOP mRNA was assayed in DU145 cells transfected with 2 different control siRNAs or 4 different SPOP siRNAs using real-time RT-PCR. These results showed that the SPOP siRNA but not the control siRNA reduced relative expression of SPOP mRNA in these cells. Further, loss of SPOP function resulted in increased expression of hedgehog target genes PTCH1, and GLI1 in 22Rv1, DU145, and RWPE cells transfected with control and SPOP siRNA.

Figure 5:
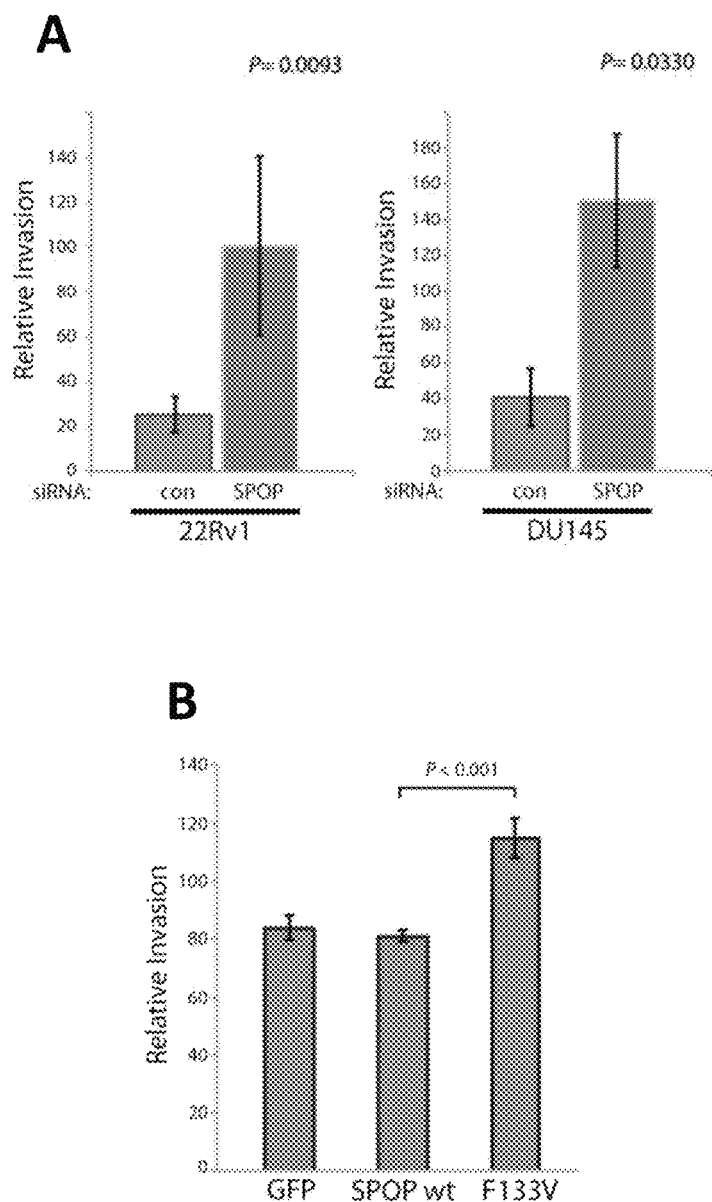
FIG. 5A-B. (A) Quantitation of invaded cells transfected with SPOP siRNA. (B) Quantitation of invaded DU145 cells transfected with GFP, SPOP wt, and SPOP F133V.

Prostate cancer cells transfected with the most common SPOP mutant (F133V) or SPOP siRNA showed increased invasion compared to controls (FIG. 5A-B), but cell growth and viability were largely unaffected. These experiments raise the possibility that cancer-associated SPOP mutations may exert a loss-of-function or dominant negative effect in prostate cancer, perhaps through altered ubiquitylation and proteosomal degradation of key protein substrates.

Example 4

SPOP Mutant Tumors are Enriched for Recurrent Somatic Deletions

A. Materials and Methods
Laser Capture Microdissection (LCM)

Five (5) µm-thick tissue sections were cut, fixed and stained on membrane coated slides followed by dissection with the ArcturusXT™ LCM Instrument (Life Technologies Corporation, California, USA). Tissue staining and LCM were performed as described by Espina et al. (ESPINA (2006)). A combined IR capture and UV laser cutting was carried out to best recover a precise subset of cells. DNA was amplified as suggested by manufacturer with the Whole Genome Amplification kit (WGA4) for single cell approach (Sigma Aldrich, St. Louis, Mo., USA). Standard PCR was used for targeted enrichment of SPOP exon 6 and 7 followed by Sanger sequencing.

FISH

The ETS rearrangement status and PTEN deletion status was assessed on tissue slides from the same tumor nodule used for RNA and DNA extraction. Methods for fluorescence in situ hybridization (FISH) for TMPRSS2-ETS gene fusion have been previously described (PERNER (2006), TOMLINS (2005)). Assays for ERG, ETV1, ETV4, and ETV5 break-apart FISH were used to confirm gene rearrangement on the DNA level (SVENSSON (2011)). To assess the status of PTEN, a locus specific probe and a reference probe were used as previously described (BERGER (2011)). The FISH probes are listed in Table 6.

TABLE 6

BAC probes used for FISH

| Assay | BAC |
|---|---|
| ERG break-apart | |
| 5' probe | RP11-372O17 |
| 3' probe | RP11-24A11 |
| ETV1 break-apart | |
| 5' probe | RP11-661L15 |
| 3' probe | RP11-79G16 |
| ETV4 break-apart | |
| 5' probe | RP11-147C10 |
| 3' probe | CTD-3215I16 |
| ETV5 break-apart | |
| 5' probe | RP11-822O23 |
| 3' probe | RP11-480B15 |
| PTEN deletion | |
| PTEN probe | CTD-2047N14 |
| Reference probe | RP11-431P18 |

Immunohistochemistry (IHC)

ERG rearrangement status was confirmed by immunohistochemistry as previously described (PARK (2010)). Briefly, primary rabbit monoclonal antibody was obtained from Epitomics (Burlingame, Calif.). Antigen recovery was conducted using heat retrieval and CC1 standard, a high pH Tris/borate/EDTA buffer (VMSI, catalog no. 950-124). Slides were incubated with 1:100 of the ERG primary antibody for 1 hour at room temperature. Primary antibody was detected using the ChromoMap DAB detection kit (VMSI, catalog no. 760-159) and UltraMap anti-Rb HRP (VMSI, catalog no. 760-4315). The anti-Rb HRP secondary antibody was applied for 16 minutes at room temperature. Slides were counterstained with Hematoxylin II (VMSI, catalog no. 790-2208) for 8 minutes followed by Bluing Reagent (VMSI, catalog no. 760-2037) for 4 minutes at 37° C. Subjective evaluation of ERG protein expression was scored as positive or negative by study pathologists.

B. Results

Tumors with SPOP mutations are ERG Fusion Negative

Figure 6:
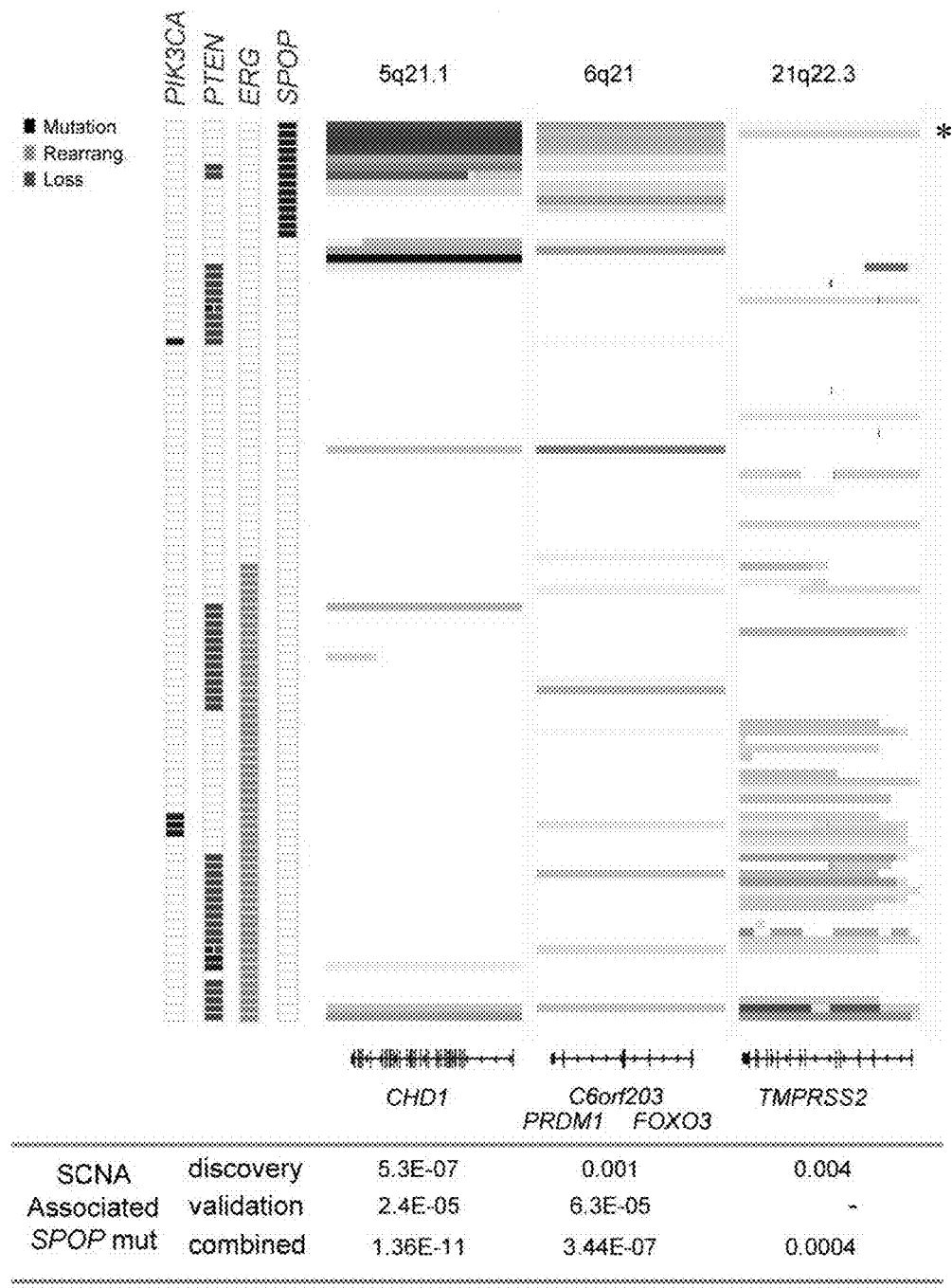
FIG. 6. SPOP defines a distinct genetic subclass of prostate cancer. Heatmap showing selected recurrent somatic copy number aberrations (SCNA). Each row represents a single prostate cancer sample of the specified genomic loci. Gray represents copy number loss (with the single exception of a copy number gain at the site marked with *) and white represents normal copy number. Samples are annotated for mutations in SPOP, PTEN, and PIK3CA, deletions of PTEN, and ERG rearrangements. Deletions at 5q21, 6q21 and 21q22.3 associated with SPOP mutation are shown. P-values of peak association with SPOP mutation in both discovery and validation cohorts are displayed at bottom (Fisher's exact test). The intron/exon structure for genes of interest is shown in their location below each region. Genomic regions are not to scale; full coordinates available in Table 7.

All exomes with SPOP mutations lacked the TMPRSS2-ERG fusion or other ETS rearrangements (FIG. 6, left panel; FIG. 7), present in up to 50% of prostate cancers (TOMLINS (2005), MOSQUERA (2009)). This mutually exclusive relationship between SPOP mutation and ERG rearrangement (P<0.001, Fisher's exact test) was confirmed in evaluable samples across all cohorts (FIG. 8A), even within an individual prostate tumor.

Figure 8:
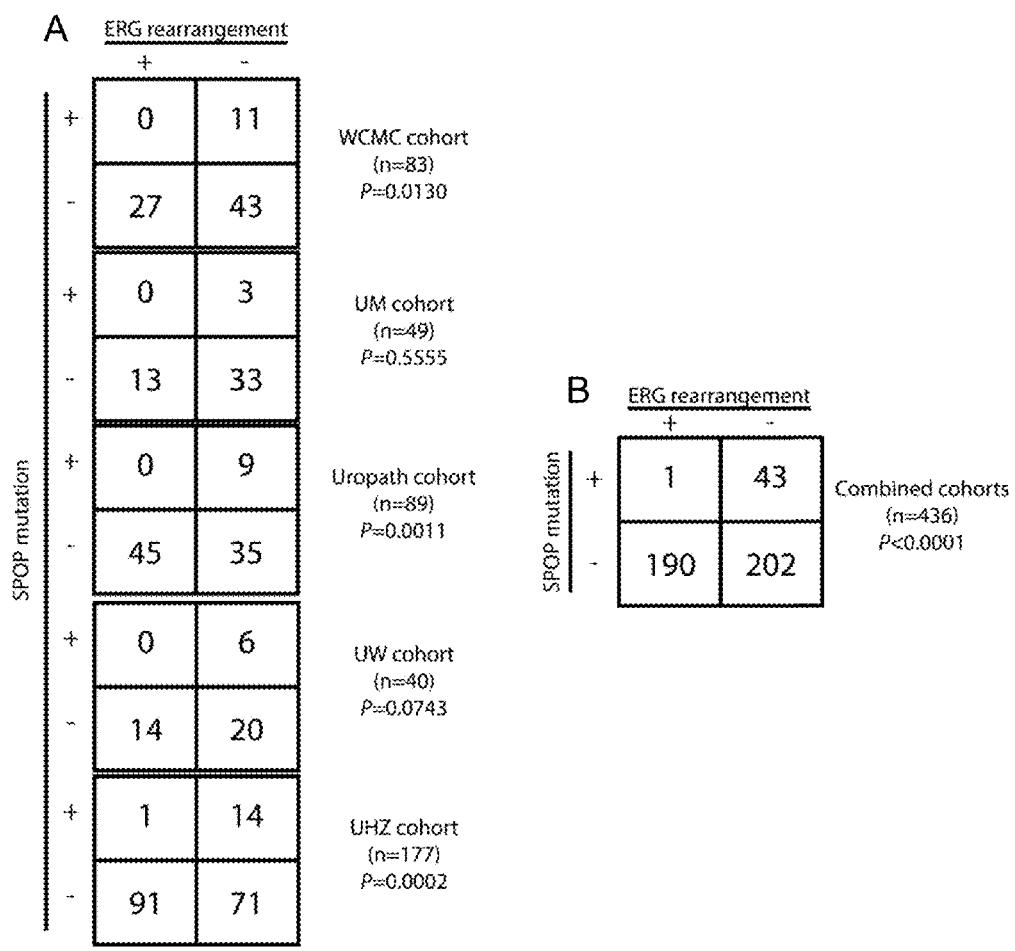
FIGS. 8A-B. Tumors with SPOP mutation lack ERG rearrangements across multiple cohorts. Relationship of SPOP mutation and ERG rearrangement is shown for individual cohorts in (A) and summarized for the whole study in (B). ERG rearrangement was determined by FISH and IHC.

A single tumor was originally classified as positive for both SPOP mutation and TMPRSS2-ERG fusion (FIG. 8B). Interestingly, re-analysis of this case using LCM followed by Sanger sequencing, revealed two morphologically distinct tumors in the sample. Microscopy of this tumor sample showed two distinct foci of prostate adenocarcinoma on an H&E stained slide of frozen tissue. One tumor had a Gleason score of 3+4=7, was ERG-negative by immunohistochemistry without ERG rearrangement by FISH, and had an F133V SPOP-mutation. The other tumor had a Gleason score of 3+3=6, was ERG-positive by immunohistochemistry with ERG-rearrangement by FISH, and had the SPOP wild-type sequence. Therefore, the mutual exclusivity of these events is recapitulated in two tumor foci from a single prostate.

Thus, SPOP mutation and ETS fusions may represent early and divergent driver events in prostate carcinogenesis. SPOP mutations were identified in LCM-analyzed high-grade intraepithelial neoplasia (HG-PIN) adjacent to invasive adenocarcinoma, and demonstrated F133V SPOP-mutation in both adenocarcinoma and HGPIN, further strengthening the premise that SPOP mutation comprises an early event in prostate tumorigenesis.

Co-occurring Genomic Alterations

In light of prior studies suggesting that prostate cancer may be classified by co-occurring genomic alterations (TAYLOR (2010), DEMICHELIS (2009), LAPOINTE (2007)), SPOP-mutant tumors were investigated for enrichment of other genomic lesions. Recurrent somatic deletions at 5q21 and 6q21 were enriched in SPOP-mutant tumors (P=1.4×$10^{-11}$ and P=3.4×$10^{-7}$, respectively, Fisher's exact test) both in the whole exome cohort and an independent prostate cancer collection (FIG. 6, Table 7). FIG. 6 shows a heatmap with selected recurrent somatic copy number aberrations (SCNA). Each row represents a single prostate cancer sample at the specified genomic loci. Samples are annotated for mutations in SPOP, PTEN and PIK3CA; deletions of PTEN; and ERG rearrangements. Deletions at 5q21, 6q21 and 21q22.3 associated with SPOP mutation are shown. Gray shading indicates copy number loss except in the one tumor sample marked with an *, which indicates copy number gain at the indicated loci (in 21q22.3). P-values of peak association with SPOP mutation in both discovery and validation cohorts are displayed at bottom (Fisher's exact test). Genomic regions are not to scale and select genes encoded in those regions are shown with their exon and intron structures indicated; full coordinates available in Table 7.

Thus, loss of tumor-suppressor genes in the 5q21 and 6q21 regions may collaborate with SPOP mutation to promote tumorigenesis. The relevant 5q21 locus contains CHD1, which encodes a chromatin-modifying enzyme that also undergoes disruptive rearrangements in prostate cancer (BERGER (2011)). The 6q21 region encompasses several genes including FOXO3, a FOXA1 homologue that has previously been implicated in prostate carcinogenesis and progression (JYANG (2009)), and PRDM1, a tumor suppressor in lymphoma (MANDELBAUM (2010)). In contrast, TP53 lesions were generally absent in SPOP-mutant tumors (P=0.015, Fisher's exact test), despite the fact that this tumor suppressor was recurrently mutated and deleted (FIG. 2). These results suggest that SPOP mutation and co-occurring deletions constitute a distinct genetic subtype of ETS-negative cancers.

Distinct genomic lesions also co-occurred with the TMPRSS2-ERG fusion. PTEN mutation or deletion was significantly associated with ERG rearrangement (P=0.00042) (FIG. 6), consistent with reports of collaboration between these two oncogenic events in mouse models (CARVER (2009), KING (2009)). Tumors with ERG rearrangement were also enriched for p53 lesions (P=0.000025) (FIG. 6). This relationship is consistent with other primary prostate cancer datasets (P=0.0044) (TAYLOR (2010), DEMICHELIS (2009)).

TABLE 7

Somatic copy number alterations associated with SPOP mutations

| Type | Cytoband | Area Coordinates (hg18) | Peak Coordinates (hg18) | q.values | Association with SPOP mutation (discovery set) | | Association with SPOP mutation (validation set) | | Association with SPOP mutation (combined) | |
|---|---|---|---|---|---|---|---|---|---|---|
| | | | | | P-value | Odds ratio | P-value | Odds ratio | P-value | Odds ratio |
| Del | 6q15 | chr6: 84993071-90693659 | chr6: 89844069-89854517 | 7.60E−14 | 0.0000 | 49.0936 | 0.0494 | 4.6152 | 0.0000 | 14.9182 |
| Del | 5q14.3 | chr5: 86736848-92949317 | chr5: 90698354-90718446 | 4.76E−06 | 0.0000 | 28.9982 | 0.0023 | 10.5654 | 0.0000 | 18.5816 |
| Del | 6q21 | chr6: 102623781-118338352 | chr6: 107452805-107484929 | 2.72E−12 | 0.0000 | 30.1055 | 0.0003 | 14.5979 | 0.0000 | 23.0189 |
| Del | 5q21.1 | chr5: 96540739-99903527 | chr5: 98211239-98298151 | 6.24E−17 | 0.0000 | 26.1837 | 0.0000 | 23.6731 | 0.0000 | 26.5255 |
| Del | 5q21.1 | chr5: 98288994-100177733 | chr5: 99892827-99956161 | 1.12E−11 | 0.0001 | 13.0406 | 0.0006 | 11.2936 | 0.0000 | 12.8012 |
| Del | 6q14.1 | chr6: 79992719-89377471 | chr6: 82929067-83023893 | 3.50E−10 | 0.0001 | 10.9692 | 0.0427 | 4.4101 | 0.0000 | 7.6868 |
| Del | 5q21.3 | chr5: 100266177-130524037 | chr5: 108694667-108775892 | 2.46E−06 | 0.0012 | 7.4120 | 0.0001 | 20.5115 | 0.0000 | 10.8653 |
| Del | 6q13 | chr6: 71718724-79638241 | chr6: 74188319-74228252 | 6.62E−05 | 0.0017 | 6.8441 | 0.2702 | 2.4264 | 0.0015 | 4.4487 |
| Del | 21q22.3 | chr21: 41569692-42033506 | chr21: 41754509-41805040 | 3.20E−13 | 0.0043 | 0.0000 | 0.1836 | 0.0000 | 0.0004 | 0.0000 |
| Del | 5q11.2 | chr5: 54500232-57785740 | chr5: 55428291-55450265 | 3.84E−08 | 0.0044 | 5.4502 | 0.0107 | 7.6381 | 0.0004 | 4.9509 |
| Amp | 8q24.3 | chr8: 142130394-143948850 | chr8: 143649163-143686346 | 0.005918 | 0.0104 | 4.7801 | 0.4292 | 0.3188 | 0.1905 | 1.9013 |
| Del | 17p13.1 | chr17: 7099211-7923319 | chr17: 7723851-7759444 | 2.24E−07 | 0.0157 | 0.1101 | 0.6699 | 0.4090 | 0.0089 | 0.1662 |
| Del | 2q21.1 | chr2: 114430192-140707944 | chr2: 131673017-131764875 | 0.0027275 | 0.0179 | 5.1272 | 0.0191 | 6.0238 | 0.0007 | 5.6709 |
| Del | 3p13 | chr3: 70098695-73514455 | chr3: 71884403-71891255 | 2.46E−06 | 0.0188 | 0.0000 | 0.6731 | 0.4708 | 0.0179 | 0.1198 |
| Amp | 21q21.1 | chr21: 18980067-18997817 | chr21: 18980170-18994744 | 0.024377 | 0.0279 | 7.9899 | 1.0000 | 0.0000 | 0.1440 | 2.9523 |
| Amp | 3q22.3 | chr3: 138503860-138525897 | chr3: 138503876-138514781 | 0.0046072 | 0.0284 | 3.8842 | 1.0000 | 1.0223 | 0.1342 | 2.3893 |
| Amp | 7q11.23 | chr7: 71946015-71962929 | chr7: 71948417-71962425 | 0.076891 | 0.0333 | 4.1148 | 0.6154 | 1.7416 | 0.0554 | 2.9006 |
| Amp | 7q21.2 | chr7: 91212265-91215184 | chr7: 91212282-91215163 | 0.059607 | 0.0333 | 4.1148 | 0.6154 | 1.7416 | 0.0554 | 2.9006 |
| Del | 2q23.3 | chr2: 151939541-152050232 | chr2: 151970139-152045679 | 0.074786 | 0.0349 | 4.8599 | 0.6500 | 1.4242 | 0.0829 | 2.9745 |
| Del | 17q21.31 | chr17: 39091591-40194083 | chr17: 39820952-39945190 | 1.17E−05 | 0.0366 | 0.0000 | 0.1836 | 0.0000 | 0.0026 | 0.0000 |
| Amp | 7p15.2 | chr7: 26355665-26394413 | chr7: 26356137-26393733 | 0.059607 | 0.0435 | 3.7332 | 0.5879 | 2.2144 | 0.0554 | 2.9006 |

Somatic Copy Number Alteration at the SPOP Locus

Figure 9:
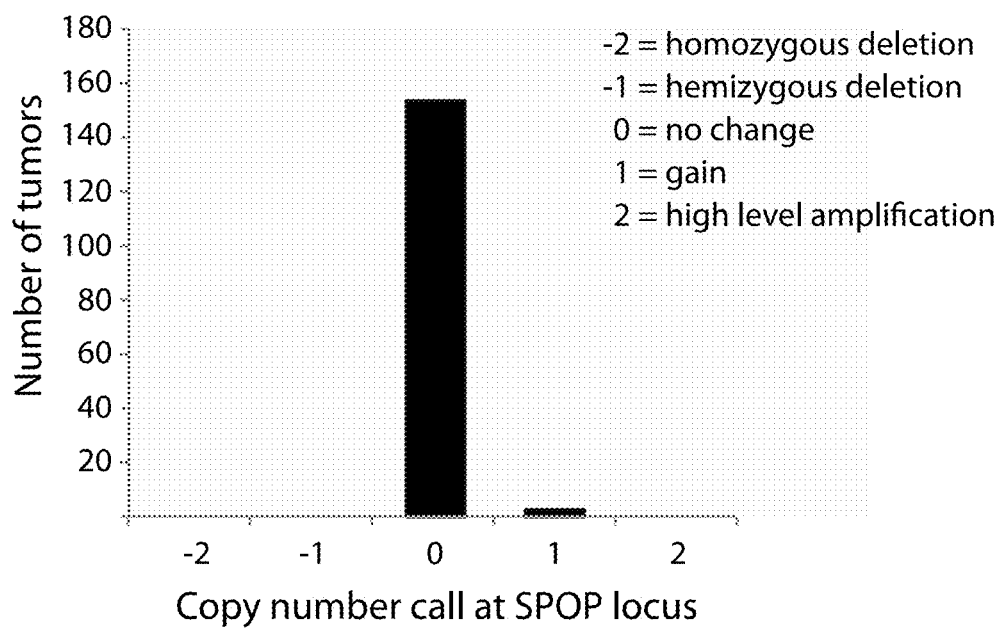
FIG. 9. Minimal changes in SPOP copy number in primary prostate cancer. Discrete copy number calls at SPOP locus in 157 primary prostate cancers, from a publicly available dataset (www.cbioportal.org/cgx/).
Figure 10:
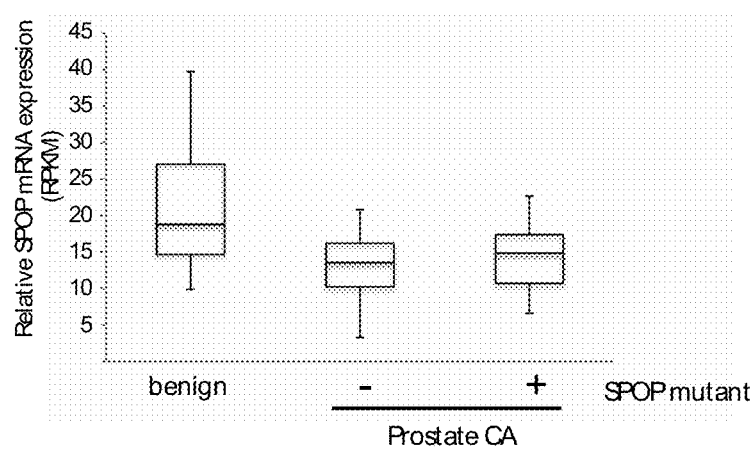
FIG. 10. SPOP is not upregulated in prostate cancer. SPOP mRNA expression measured by RNA-seq in 6 benign prostate samples and 53 prostate cancers (7 SPOP mutant, 46 SPOP wt). Relative expression is displayed as reads per kilobase per million mapped reads (RPKM).

Previous reports indicate that SPOP may function as an oncogene based on genomic amplifications in other cancers (KAN (2010)) and protein overexpression in clear cell renal cell carcinomas (LIU (2009)). However, minimal somatic copy number aberrations were seen in the SPOP locus in primary prostate cancers from multiple cohorts, with no evidence of deletions in tumors with SPOP mutations (FIG. 9) (TAYLOR (2010)). In addition, in 6 benign prostate samples and 53 prostate cancers (7 SPOP mutant, 46 SPOP wt), SPOP mRNA expression measured by RNA-seq was not up-regulated in prostate cancer samples from multiple cohorts, but was more frequently down-regulated compared to benign controls (FIG. 10). We therefore conclude that the biological effect of SPOP mutations is not recapitulated by somatic copy number alterations in primary prostate cancer.

Relative Lack of PTEN and PIK3CA Lesions in SPOP Mutant Prostate Cancers

Figure 11:
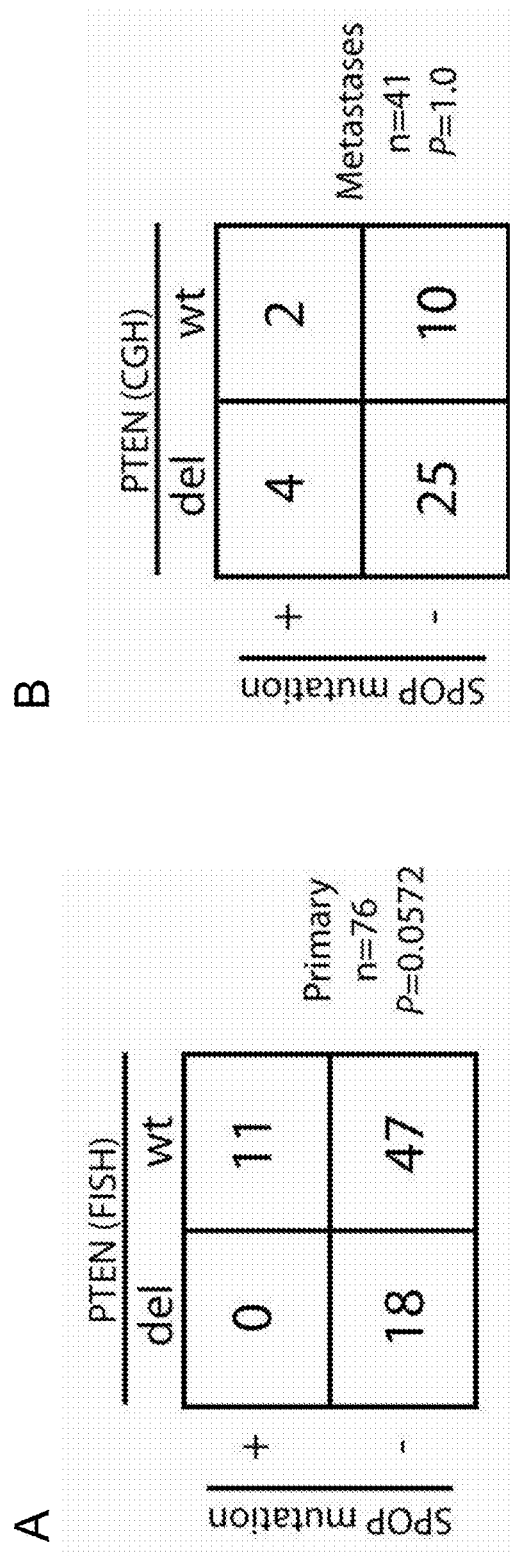
FIG. 11. Tumors with SPOP mutation lack PTEN deletion in primary but not metastatic prostate cancer. (A) Relationship of SPOP mutation and PTEN deletion determined by FISH in primary prostate cancers from the WCMC cohort. (B) Relationship of SPOP mutation and PTEN deletion determined by CGH in prostate cancer metastases from the UW cohort

SPOP mutations showed an inverse relationship with mutation and/or copy number loss at the PTEN locus in primary tumors (P=0.044) (FIG. 6); this trend was supported by FISH analysis for PTEN deletion (FIG. 11A). Furthermore, the p110α gene PIK3CA, which antagonizes the lipid phosphatase activity of PTEN, was not mutated in SPOP-mutant tumors (FIG. 6). In total, SPOP mutation showed an inverse relationship with lesions of PTEN and PIK3CA (P=0.040) in primary tumors. However, metastatic tumors showed no such inverse relationship, with SPOP mutations and PTEN deletions identified together in metastases (FIG. 11B). This finding may reinforce that SPOP mutation is an early event, with PTEN deletion and other activating lesions in the PI3K pathway more representative of steps in progression of disease.

REFERENCES

The references cited in this application are as follows:
BENJAMINI, J. Roy. Statist. Soc. 57, 289 (1995)
BERGER et al., Nature 470, 214 (2011)
BHATIA-GAUR et al., Genes Dev. 13, 966 (1999)
BOORMANS et al., Br J Cancer 102(10), 1491-4 (2010)
C. I. G. A. R. Network, Nature 474, 609 (2011)
CAIRNS et al., Cancer Res. 57, 4997 (1997)
CARVER et al., Nat. Genet. 41, 619 (2009)
CHAPMAN et al., Nature 471, 467 (2011)
CIBULSKIS et al., Bioinformatics 27, 2601 (2011)
CONSORTIUM, Nucleic Acids Res. 39, D214 (2011)
DASKIVICH et al., Cancer 117, 2058 (2011)
DEMICHELIS et al., Genes Chromosomes Cancer 48, 366 (2009)
DEPRISTO et al., Nat. Genet. 43, 491 (2011)
ESPINA et al., Nat. Protoc. 1, 586 (2006)
FISHER et al., Genome Biol. 12, R1 (2011)
FORBES et al., Nucleic Acids Res. 39, D945 (2011)
FUJITA et al., Nucleic Acids Res. 39, D876 (2011)
GAO et al., Epigenetics 5, 100 (2010)
GETZ et al., Science 317, 1500 (2007)
GRIFFITH et al., Nucleic Acids Res. 36, D107 (2008)
HE et al., Genomics 43, 69 (1997)
JEMAL et al., CA Cancer J Clin 61, 69 (2011)
JYANG et al., Clin Cancer Res 15, 752 (2009)
KAN et al., Nature 466, 869 (2010)
KIBEL et al., Cancer Res. 63, 2033 (2003)
KIM et al., Genome Res. 21, 1028 (2011)
KING et al., Nat. Genet. 41, 524 (2009)
KOZOMARA, et al., Nucleic Acids Res. 39, D152 (2011)
KUMAR et al., Proc. Natl. Acad. Sci. U.S.A. 108, (2011)
LAPOINTE et al., Cancer Res. 67, 8504 (2007)
LI et al., Bioinformatics 25, 1754 (2009)
LI et al., Science 275, 1943 (1997)
LINJA et al., J. Steroid Biochem. Mol. Biol. 92, 255 (2004)
LIU et al., Science 323, 1218 (2009)
MAJUMDER et al., Cancer cell 14, 146 (2008)
MANDELBAUM et al., Cancer Cell 18, 568 (2010)
MCKENNA et al., Genome Res. 20, 1297 (2010)

MOSQUERA et al., *Clin. Cancer Res.* 15, 4706 (2009)
NAGAI et al., *FEBS Lett.* 418, 23 (1997)
PARK et al., *Neoplasia* 12, 590 (2010)
PERNER et al., *Cancer Res.* 66, 8337 (2006)
PFLUEGER et al., *Genome Res.* 21, 56 (2011)
QUAIL et al., *Nat. Methods* 5, 1005 (2008)
REICH et al., *Nat. Genet.* 38, 500 (2006)
ROBINSON et al., *Nat. Biotechnol.* 29, 24 (2011)
RUBIN et al., *Clin. Cancer Res.* 6, 1038 (2000)
SHERRY et al., *Nucleic Acids Res.* 29, 308 (2001)
STRANSKY et al., *Science* 333, 1157 (2011)
SVENSSON et al., *Lab. Invest.* 91, 404 (2011)
TAYLOR et al., *Cancer Cell* 18, 11 (2010)
TOMLINS et al., *Nature* 448, 595 (2007)
TOMLINS et al., *Science* 310, 644 (2005)
VISAKORPI et al., *Nat. Genet.* 9, 401 (1995)
ZHUANG et al., *Mol. Cell.* 36, 39 (2009)

---

We claim:

1. A method comprising detecting a SPOP mutation in a prostate sample using a nucleic acid-based assay, wherein said SPOP mutation is a missense mutation at an amino acid position that is in the MATH domain of SPOP and responsible for substrate binding selected from the group consisting of Y87, F102, 5119, K129, W131, and K134.

2. The method of claim 1, wherein said prostate sample is prostate tissue, urine, semen, a prostatic secretion, or prostate cells.

3. The method of claim 1, wherein the SPOP mutation is detected by (a) amplifying nucleic acid comprising SPOP in said prostate sample, and (b) sequencing the amplified nucleic acid to identify the presence of a mutation.

4. The method of claim 3, wherein said amplifying comprises amplifying the MATH domain of SPOP.

5. The method of claim 1, which comprises detecting said mutation in situ.

6. The method of claim 1, which comprises obtaining nucleic acid from said prostate sample and detecting a SPOP mutation by a microarray-based assay or by an RT-PCR-based assay.

7. The method of claim 1 which further comprises detecting the presence or absence of one or more co-occurring genomic alterations.

8. The method of claim 7 wherein said genomic alterations are selected from the group consisting of the absence of a PTEN mutation or the absence of PTEN copy number loss.

9. The method of claim 8 wherein said genomic alterations are the presence of a 5q21 deletion, the presence of a 6q21 deletion or the absence of an ETS-rearrangement, or any combination thereof.

10. The method of claim 7, wherein said prostate sample is prostate tissue, urine, semen, a prostatic secretion or prostate cells.

11. The method of claim 1, wherein the SPOP mutation is selected from the group consisting of S119N, K134N, Y87N, W131G, K129E, and F102C.

12. A method comprising detecting a SPOP mutation in a prostate sample using a nucleic acid-based assay, wherein said SPOP mutation is a missense mutation at the amino acid position F133 that is in the MATH domain of SPOP and responsible for substrate binding.

13. The method of claim 12, wherein said prostate sample comprises prostate tissue or prostate cells.

14. The method of claim 12, wherein the SPOP mutation is detected by (a) amplifying nucleic acid comprising SPOP in said prostate sample, and (b) sequencing the amplified nucleic acid to identify the presence of a mutation.

15. The method of claim 14, wherein said amplifying comprises amplifying the MATH domain of SPOP.

16. The method of claim 12, which comprises obtaining nucleic acid from said prostate sample and detecting a SPOP mutation by a microarray-based assay.

17. The method of claim 12 which further comprises detecting the presence or absence of one or more co-occurring genomic alterations.

18. The method of claim 17, wherein said genomic alterations are selected from the group consisting of the absence of a PTEN mutation or the absence of PTEN copy number loss.

19. The method of claim 17, wherein said genomic alterations comprise the absence of an ETS-rearrangement.

20. The method of claim 17, wherein said prostate sample is prostate tissue.

21. The method of claim 12, wherein the missense mutation is F133V.

* * * * *